United States Patent
Concannon et al.

(12) 
(10) Patent No.: US 6,458,534 B1
(45) Date of Patent: Oct. 1, 2002

(54) GENE ASSOCIATED WITH NIJMEGEN BREAKAGE SYNDROME, IT'S GENE PRODUCT AND METHODS FOR THEIR USE

(75) Inventors: Patrick J. Concannon, Bainbridge Island; Christine S. Vissinga; Karen M. Cerosaletti, both of Seattle, all of WA (US); Raymonda Varon-Mateeva, Berlin (DE); Karl Sperling, Berlin (DE); André Wiesmann da Silva Reis, Berlin (DE)

(73) Assignee: Virginia Mason Research Center, Seattle, WA (US)

( * ) Notice: Subject to any disclaimer, the term of this patent is extended or adjusted under 35 U.S.C. 154(b) by 0 days.

(21) Appl. No.: 09/300,008

(22) Filed: Apr. 27, 1999

Related U.S. Application Data
(60) Provisional application No. 60/083,269, filed on Apr. 27, 1998.

(51) Int. Cl.$^7$ .......................... C12Q 1/68; C07H 21/02
(52) U.S. Cl. ........................................ 435/6; 536/22.1
(58) Field of Search .................. 435/6, 91.2; 536/22.1, 536/23.1

(56) References Cited

PUBLICATIONS

GenBank Entrez accession No. AF0513334 (human NBS mRNA); May 9, 1998.
GenBank Entrez accession No. AF049895 (human 8q21.3: NBS1, DECR and CALB1 genes), Jan. 21, 1999.
http://ftp.genome.washington.edu/RM/RepeatMasker.html.
Altschul et al., 1990, "Basic Local Alignment Search Tool", J. Mol. Biol. 215:403–410.
Beckmann et al., 1998, "Merging Extracellular Domains: Fold Prediction for Laminin G–Like and Amino–Terminal Thrombospondin–Like Modules Based on Homology to Pentraxins", J. Mol. Biol. 275:725–730.
Bork et al., 1997, "A Superfamily of Conserved Domains in DNA Damage–Responsive Cell Cycle Checkpoint Proteins", FASEB J. 11:68–76.
Cerosaletti et al., 1998, "Fine Localization of the Nijmegen Breakage Syndrome Gene to 8q21: Evidence for a Common Founder Haplotype", Am. J. Hum. Genet. 63:125–134.
Chrzanowska et al., 1995, "Eleven Polish Patients with Microcephaly, Immunodeficiency, and Chromosomal Instability: The Nijmegen Breakage Syndrome", Am. J. Med. Genet. 57:462–471.
Concannon and Gatti, 1997, "Diversity of ATM Gene Mutations Detected in Patients with Ataxia–Telangiectasia", Hum. Mutat. 10:100–107.
Digweed, 1993, "Human Genetic Instability Syndromes: Single Gene Defects with Increased Risk of Cancer", Toxicol. Lett. 67:259–281.

Hofmann and Bucher, 1995. "The FHA Domain: A Putative Nuclear Signalling Domain Found in Protein Kinases and Transcription Factors", TIBS 20:347–349.
Hudson et al., 1995, "An STS–Based Map of the Human Genome", Science 270:1945–1954.
Jaspers et al., 1988, "Genetic Complementation Analysis of Ataxia Telangiectasia and Nijmegen Breakage Syndrome: A Survey of 50 Patients", Cytogenet. Cell Genet. 49:259–263.
Jaspers et al., 1988, "Patients with an Inherited Syndrome Characterized by Immunodeficiency, Microcephaly, and Chromosomal Instability: Genetic Relationship to Ataxia Telangiectasia", Am. J. Hum. Genet. 42:66–73.
Jongmans et al., 1997, "Nijmegen Breakage Syndrome Cells Fail to Induce the p53–Mediated DNA Damage Response following Exposure to Ionizing Radiation", Mol. Cell Biol. 17:5016–5022.
Komatsu et al., 1996, "Gene for Nijmegen Breakage Syndrome (V2) Is Not Located on Chromosome 11", Am. J. Hum. Genet. 58:885–888.
Matsuura et al., 1998, "Radiation Induction of p53 in Cells from Nijmegen Breakage Syndrome Is Defective but Not Similar to Ataxia–Telangiectasia", Biochem. Biophys. Res. Comm. 242:602–607.
Orita et al., 1989, "Rapid and Sensitive Detection of Point Mutations and DNA Polymorphisms Using the Polymerase Chain Reaction", Genomics 5:874–879.
Pearson and Lipman, 1988, "Improved Tools for Biological Sequence Comparison", Proc. Natl. Acad. Sci. USA 85:2444–2448.
Platzer et al., 1997, "Ataxia–Telangiectasia Locus: Sequence Analysis of 184 kb of Human Genomic DNA Containing the Entire ATM Gene", Genome Res. 7:592–605.
Saar et al., 1997, "The Gene for the Ataxia–Telangiectasia Variant, Nijmegen Breakage Syndrome, Maps to a 1–cM Interval on Chromosome 8q21", Am. J. Hum. Genet. 60:605–610.
Savitsky et al., 1995, "A Single Ataxia Telangiectasia Gene with a Product Similar to PI–3 Kinase", Science 268:1749–1753
Savov et al., 1992, "High Percentage Acrylamide Gels Improve Resolution in SSCP Analysis", Nucl. Acids Res. 20:6741–6742.
Schuler et al., 1996, "A Gene Map of the Human Genome", Science 274:540–546.

(List continued on next page.)

*Primary Examiner*—Eggerton A. Campbell
(74) *Attorney, Agent, or Firm*—Townsend and Townsend and Crew LLP

(57) ABSTRACT

The present invention relates to a novel gene, NBS1, and its gene product, nibrin. In addition, it relates to methods for detecting mutations or polymorphisms of the gene that are associated with Nijmegen breakage syndrome in patients. Such mutations may be used to diagnose a predisposition to the development of certain pathological conditions in these patients.

10 Claims, 9 Drawing Sheets

OTHER PUBLICATIONS

Figure 1A:
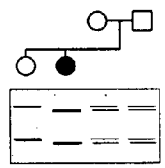

Schuler et al., 1991, "A Workbench for Multiple Alignment Construction and Analysis", Proteins 9:180–190.

Seyschab et al., 1992, "Simultaneous Measurement, Using Flow Cytometry, of Radiosensitivity and Defective Mitogen Response in Ataxia Telangiectasia and Related Syndromes", Eur. J. Pediatr. 151:756–760.

Shilo and Weinberg, 1981, "DNA Sequences Homologous to Vertebrate Oncogenes Are Conserved in *Drosophila melanogaster*", Proc. Natl. Acad. Sci. USA 78:6789–6792.

Shiloh, 1997, "Ataxia–Telangiectasia and the Nijmegen Breakage Syndrome", Annu. Rev. Genet. 31:635–662.

Stumm et al., 1997, "Noncomplementation of Radiation–Induced Chromosome Aberrations in Ataxia–Telangiectasia/Ataxia–Telangiectasia Variant Heterodikaryons", Am. J. Hum. Genet. 60:1246–1251.

Taalman et al., 1983, "Hypersensitivity to Ionizing Radiation, in vitro, in a New Chromosomal Breakage Disorder, the Nijmegen Breakage Syndrome", Mutation Res. 112:23–32.

van der Burgt et al., 1996, "Nijmegen Breakage Syndrome", J. Med. Genet. 33:153–156.

Varon et al., 1998, "Nibrin, a Novel DNA Double–Strand Break Repair Protein, Is Mutated in Nijmegen Breakage Syndrome", Cell 93:467–476.

Wegner et al., 1988, "A New Chromosomal Instability Disorder Confirmed by Complementation Studies", Clin. Genetics 33:20–32.

Fig. 2A.

```
1                                                                            METTRPLYSLEULEUPROALAALAGLYPROALAGLY    12
  GCCCCAGCCCTGAGGAGCCGGACCGGATGCGAAACTGCTGCCGCCGCCGGGCCCGGCAGGA                                                      61
  GLYGLUPROTYRARGLEULEUTHRGLYLVALGLUTYRVALVALGLYARGLYSASNCYSALAILE                                                   33
  GGAGAACCATACAGACTTTGACTGGCGTTGAGTACGTTGTTGGAAGGAAACTGCTGCCATT                                                     124
  LEUILEGLUASNASPGLNSERILESERARGASNHISALAVALLEUTHRALAASNPHESERVAL                                                    54
2 CTGATTGAAAATGATCAGTCGATCAGCCGAAATCATGCTGTTAACTGCTGCTACTTTCTGTA                                                    187
  THRASNLEUSERGLNTHRASPGLUILEPROVALLEUTHRLEULYSASPASNSERLYSTYRGLY                                                    75
  ACCAACCTGAGTCAAACAGATGAAATCCCTGTATTGACATTAAAGATAATCTAAGTATGGT                                                     250
  THRPHEVALASNGLYLUGLULYSMETGLNASNGLYPHESERARGTHRLEULYSSERGLYASPGLY                                                  96
3 ACCTTTGTTAATGAGAAAAATGCAGAATGCTTTCCGAACTTTGAAGTGGGGATGGT                                                          313
  ILETHRPHEGLYVALPHEGLYSERLYSPHEARGILEGLUTYRGLUPROLEUVALALACYSSER                                                   117
  ATTACTTTTGCAGTGTTTGGAAGTAAATCAGAATAGAGTATGAGCCTTTGTTGCATGCTCT                                                     376
  SERCYSLEUASPVALSERGLYLYSTHRALALEUASNGLNALAILELEUGLNLEUGLYLYPHE                                                    138
4 TCTTGTTTAGATGTCTCTGGGAAACTGCTTTAAATCAAGCTATATTGCAACTTGGAGGATTT                                                    439
  THRVALASNASNTRPTHRGLUGLUCYSTHRHISLEUVALMETVALSERVALLYSVALTHRILE                                                   159
  ACTGTAAACAATTGGACAGAAGAATGCACACTCACCTTGTCATGGTATCAGTGAAAGTTACCATT                                                  502
  LYSTHRLLECYSALALEUILECYSGLYARGPROILEVALLYSPROGLUTYRPHETHRGLUPHE                                                   180
  AAAACAATATGTGCACTCATTGTGGACGTCCAATTGTAAAGCCAGAATATTTACTGAATTC                                                     565
5 LEULYSALAVALGLUSERLYSSGLNPROPROGLNILEGLUSERPHETYRPROPROLEUASP                                                     201
  CTGAAAGCAGTTGAGTCCAAGAGCACCCCACAAGTGAAATTTTTACCCACCTCTTGAT                                                        628
  GLUPROSERILEGLYSERLYSASNVALASPLEUSERGLYARGGLNGLUARGLYSGLNILEPHE                                                   222
6 GAACCATCTATTGGAAGTAAAATGTTGATCTGTCAGGACGGCAGGAAAGAAACAAATCTTC                                                     691
  LYSGLYLYSTHRPHEILEPHELEUASNALALYSGLNHISLYSLEUSERSERALAVALVAL                                                      243
  AAAGGAAAACATTATATTTTGAATGCCAAACAGCATAAGAATTCAGTTCCGCAGTGTC                                                        754
  PHEGLYGLYGLYGLUALAARGLEUILETHRGLUGLUASNGLUGLUHISASNPHEPHELEU                                                      264
7 TTTGGAGGTGGGGAAGCCAGGTTGATAACAGAAGAGAATGAAGAACATAATTTCTTTTTG                                                      817
```

```
TTCTAGTACTAGAAAACTGAAGACCATGTGGAGACTTCATCAAACATGGGTTTAGTTTTCACCA   2959
GAATGGAAAGACCCTGTACCCCTTTTTGGTGGTCTTACTGAGCTGGGTGGGTGTCTGTTTTGAG   3022
CTTATTTAGAGTCCTAGTTTTTCCTACTTATAAAGTAGAAATGGTGAGATTGTTTTCTTTTCT   3085
ACCTTAAAGGGAGATGGTAAGAAAACAATGAATGTCTCTTTTTCAAACTTTATTGACAAGTGATT   3148
TTCAAGTCTGTGTTCAAAAATATATTCATGTACCTGTGATCCAGCAAGAAGGGAGTTCCAGTC   3211
AAGAGTCACTACAACTGATTAGTGTTTAGAGAATGAGAAATGGAACAGTGAGGAATGGAGGC   3274
CATATTCCATGACTTCCCTTGTAAACAGAAGCAACAAGGGACAAGAGGCTGGCCTCTACA   3337
TCACTCTCACCTTCCAAATCTTGTGGAAGTGCATCTACTTGCCAGAACCAAATTAACTTACTT   3400
CCAAGTTCTGGCTGCTGCAGGTGGAACTCCAGCTCCAAGGGAGTTAGGGAAATGAAGGTCTT   3463
TTTTAAAAGCTTCTCAGCCTTCCTAGGGAACAGAAATTGGGTGAGCCAATCTGCAATTCTA   3526
CTACAGGCATTGAGACCAGTTAGATTATTGAAATATTATAGAGAGTTATGAACACTTAAATTA   3589
TGATAGTGGTATGACATTGGATAGAACATGGAGTACTTTAGAAGTAGAATTGACAGGCATAT   3652
TAGTTGATGAAATGGAGTCATTTGAGTCTTCATTTACACCATGTATCATAATTACCAAGTGAAG   3715
CTGGTGGAACATATGGTCTCCACATTTACAGTTAAGGAATATAATGGACAGATTAATATTGTTC   3778
TCTGTCATGCCCACAATCCCTTTCTAAGGAAGACTGCCCTACTATAGCAGTTTTATATTTGT   3841
CAATTATGAATATAATAATGAATGAGAGTTCTGGTACCTCCTGTCTTTACAAATATTGGTGTTGT   3904
CAGTATTTTTCCTTTTTAACCATTCAAGCTGTTTCATTTGGTTTTAATT   3967
TGTATATCCCTGATATATAGCTATAATTGGGTCATAGAAATTCTTTATACATTCTAGATGCAAGTCT   4030
CTTGTCGGATATATGTATTGAGATATTACACCTAGTCTGTGGCTTGACTGTTTTCTTTGTC   4093
TTTGATGAATAGAAGTTTTAAATTTGACAAGGTCAAATTTATTTTTTCTTTTGTTTGATA   4156
TTTTTCTCTCCAATTAACCCCAAGATTTCAGATATTCGCTCTATTATATAAACTTTATAT   4219
TTTTATATTGTGATCTACCTTGAATTGATATGTTGTGAATTATGGATCAGGGTTCTTT   4282
TTTTCCCCATACAAGTATCCAGTCATTGTAACACTGTTTATTGAAAGAATTATCCTTTCCTC   4345
ATTAAATTACCTTGCCAATTAGTAAAAATCAATTAACCAT   4386
```

| | | | | | | |
|---|---|---|---|---|---|---|
| HNIBRIN | 24 | YVVGRKN......CAILIEN...DQSISRNHAVLTAN.13.VLTLKDN.SKYGTFVNE..EKMQNGFS...RTLKSGDGITFG | (SEQ ID NO: 41) |
| HKI67 | 27 | CLFGRGIE....QDIRIQL....PVVSKQHCKIEIH..2.EAILHNFSSTNPTQVNG..SVIDEP......VRLKHGDVLTII | (SEQ ID NO: 42) |
| SCDUN1 | 56 | TTIGRSRS....CDVILSE....PDIST FHAEFHLL.10.LINVIDK.SRNGTFING..NRLVKKD....YILKNGDRIVFG | (SEQ ID NO: 43) |
| SPCDS1 | 60 | WGFGRHKS....CEVVLNG....PRVSNFHFEIYQG.10.VVFLHDH.SSNGTFLNF..ERLAKNSR...TILSNGDEIRIG | (SEQ ID NO: 44) |
| SCMEK1 | 47 | VKVGRNDK..1.CQIVLTN....PSISSVHCVFWCV..8.MFYVKDC.SLNGTYLNG..LLLKRDKT...YLLKHCDVIELS | (SEQ ID NO: 45) |
| SCSPK1 | 66 | WTFGRNPA....QDYHLGN....ISRLSNKHFQILLG..3.NLLLNDI.STNGTWLNG..QKVEKNSN...QLLSQGDEITVG | (SEQ ID NO: 46) |
| SCFKH1 | 76 | VTTIGRNTD.15.IDIDLGP....AKIVSRKHAAIRFN..4.SWELQIF.GRNGAKVNE..RRIPTGPDSPPTVLQSGCIIDIG | (SEQ ID NO: 47) |
| SCFHL1 | 300 | AIIGRRSE..6.VDVNLGP....SKSISRRHAQIFYN..3.RFELSII.GKNGAFVDD..IFVEKGNT...VPLRNTKIQIG | (SEQ ID NO: 48) |
| ATKAPP | 209 | VKIGRVSP....SDIALKD....SEVSGKHAQIIWN..4.KWELVDMGSLNGTLVNS..HSISHPDL.8.VELASDDIIILG | (SEQ ID NO: 49) |
| ASFRAH | 204 | VHIGKPND..4.IDVDVSGFANSEITVSRVHADIRLE...AHYLEDVGSSNGTYINN..LPLLPGNR...HRLRPGDRISLG | (SEQ ID NO: 50) |

*Fig. 4B.*

GENE ASSOCIATED WITH NIJMEGEN BREAKAGE SYNDROME, IT'S GENE PRODUCT AND METHODS FOR THEIR USE

This application claims the benefit of U.S. Provisional Application No. 60/083,269, filed Apr. 27, 1998, which is incorporated by reference herein in its entirety.

1. INTRODUCTION

The present invention relates to a novel gene, NBS1, and its gene product, nibrin. In addition, it relates to methods for detecting mutations or polymorphisms of the gene that are associated with Nijmegen breakage syndrome in patients. Such mutations may be used to diagnose a predisposition to the development of certain pathological conditions in these patients.

2. BACKGROUND OF THE INVENTION

Nijmegen breakage syndrome (NBS), a rare autosomal recessive disorder, belongs to the group of inherited human chromosomal instability syndromes, that includes Bloom's syndrome, Fanconi's anemia and ataxia-telangiectasia (AT). All of these disorders are characterized by spontaneous chromosomal instability, immunodeficiency and predisposition to cancer, but have distinct cytogenetic features and sensitivities to specific DNA damaging agents (for review see Digweed et al., 1993, Toxicol. Lett. 67:259–281). NBS shares a number of features in common with AT, most notably, a specific sensitivity to ionizing radiation (IR) and a predisposition to malignancies, particularly lymphoid cancers. Based on these features, and the results of earlier somatic cell complementation studies, NBS has long been classified as a variant of AT (for review see: Shiloh, 1997, Annu. Rev. Genet. 31:635–662). However, NBS has been shown to be genetically distinct from AT (Cerosaletti et al., 1998, Am. J. Hum. Genet. 63:125–134) and results from mutations in a novel mammalian gene.

Clinically, NBS is characterized by developmental defects, immunodeficiency, chromosomal instability, and an increased incidence of malignancies. Developmental defects typically observed in NBS patients include a severe and progressive microcephaly, growth retardation, mild to moderate mental retardation, and primary ovarian failure. Humoral and cellular immunodeficiency with recurrent respiratory infections is a consistent finding in NBS, but patients show intra- and interfamiliar variability. The immunologic characteristics of NBS encompass both developmental defects in tissues where lymphocytes develop and cellular defects in the responses of these cells to stimuli.

NBS patients have normal karyotypes, but chromosomal abnormalities are observed in cultured lymphocytes. The most frequently observed cytogenetic aberrations are rearrangements involving chromosomes 7 and 14 as observed in AT patients (van der Burgt et al., 1996, J. Med. Genet. 33:153–156). The distribution of the breakpoints on these chromosomes is non-random and preferentially cluster around immunoglobulin and T cell receptor loci where recombination events involving double strand breaks occur during lymphoid development. Malignancies, predominantly of lymphoid origin, occur in NBS with a high frequency and at atypically young ages. The most common tumors are B-cell lymphomas.

Cultured cells from NBS patients have impaired responses to ionizing radiation including an increased frequency of chromosomal aberrations, reduced survival in colony forming assays (Taalman et al., 1983, Mutat. Res. 112:23–32; Jaspers et al., 1988, Cell Genet. 49:259–263), radio-resistant DNA synthesis (RDS) (Jaspers et al., 1988, Am. J. Hum. Genet. 42:66–73; Wegner et al., 1988, Clin. Genet. 33:20–32; Chrzanowska et al., 1995, Am. J. Med. Genet. 57:462–471), a failure to activate cell cycle checkpoints (Seyschab et al., 1992, Eur. J. Pediat. 151:756–760; Jongmans et al., 1997, Mol. Cell Biol. 17:5016–5022), and a delayed up-regulation of p53 levels (Jongmans et al., 1997; Matsuura et al., 1998, Biochem. Biophys. Res. Commun. 242:602–607). All of these features are also observed in cells from patients with AT (Shiloh, 1997, Annu. Rev. Genet. 31:635–662).

In order to understand the complex relationship between NBS and AT, cell lines from patients with these disorders have been fused and assayed for various phenotypes involving response to ionizing radiation. Complementation for RDS has been reported in AT/NBS cell hybrids (Jaspers et al., 1988; Wegner et al., 1988). However, complementation of RDS has also been observed in hybrids resulting from fusions of cells from different AT patients suggesting the existence of multiple complementation groups for AT (Jaspers et al., 1988)—a finding that has not been borne out by mutational analysis of the AT gene (ATM) (Savitsky et al., 1995, Science 268:1749–1753; Concannon and Gatti, 1997, Hum. Mutat. 10:100–107). Microcell mediated transfer of a normal copy of chromosome 11 containing the AT gene did not complement the radiation sensitivity of NBS cells suggesting that the gene mutated in NBS was not ATM (Komatsu et al., 1996, Am. J. Hum. Genet. 58:885–888). Non-complementation was also observed in AT/NBS hybrids tested for another phenotype, radiation induced chromosomal aberrations. This latter finding has been interpreted as suggesting that the products of the AT and NBS genes, although distinct, may interact in a common biochemical pathway, or may be parts of a common protein complex (Stumm et al., 1997, Am. J. Hum. Genet. 60:1246–1251).

Molecular cloning of a gene associated with NBS would facilitate the analysis of the underlying defects in NBS. While genome-wide search for linkage in NBS families localized the gene to a 1 cM region on chromosome 8q21, the large physical size of this region, and the small number of available NBS families with informative recombination events, limited further progress towards gene identification.

3. SUMMARY OF THE INVENTION

The present invention relates to a novel gene, NBS1, and its encoded product, nibrin. In particular, the invention relates to polynucleotides encoding nibrin or fragments thereof, nibrin polypeptides, antibodies to nibrin polypeptides, methods for detecting nibrin in a cell, and methods for diagnosing NBS by detecting expression levels or mutations of NBS1 gene, as well as methods of treating NBS.

The invention is based, in part, or Applicants' discovery that a novel polynucleotide isolated from a region of human chromosome 8q21 contained mutations in all NBS patients. The mutations included deletions and insertions that resulted in a frameshift as well as a point mutation. Specific mutations associated with the NBS plenotype include 657del5, 698del4, 835del4, 842insT, 1142delC, 976C>T, 681delT and 900del25. In addition, polymorphisms of the gene include 553 G/C, 1197 T/C, 2016 A/G, 102 G/A, IVS 5+9 T/C, IVS5+51delT, IVS9+18 C/T and IVS-7A/G.

It is an object of the invention to detect a mutation or polymorphism in NBS patients. A mutation includes a missense, nonsense and frameshift mutation.

It is another object of the invention of the invention to diagnose a predisposition to a pathological conditions such as cancer, microcephaly, mental retardation, and primary ovarian failure, based on detection of a mutation in the NBS1 gene disclosed herein.

It is also an object of the invention to treat NBS by replacing the mutated gene in a NBS patient.

4. BRIEF DESCRIPTION OF THE DRAWINGS

Figure 1B:
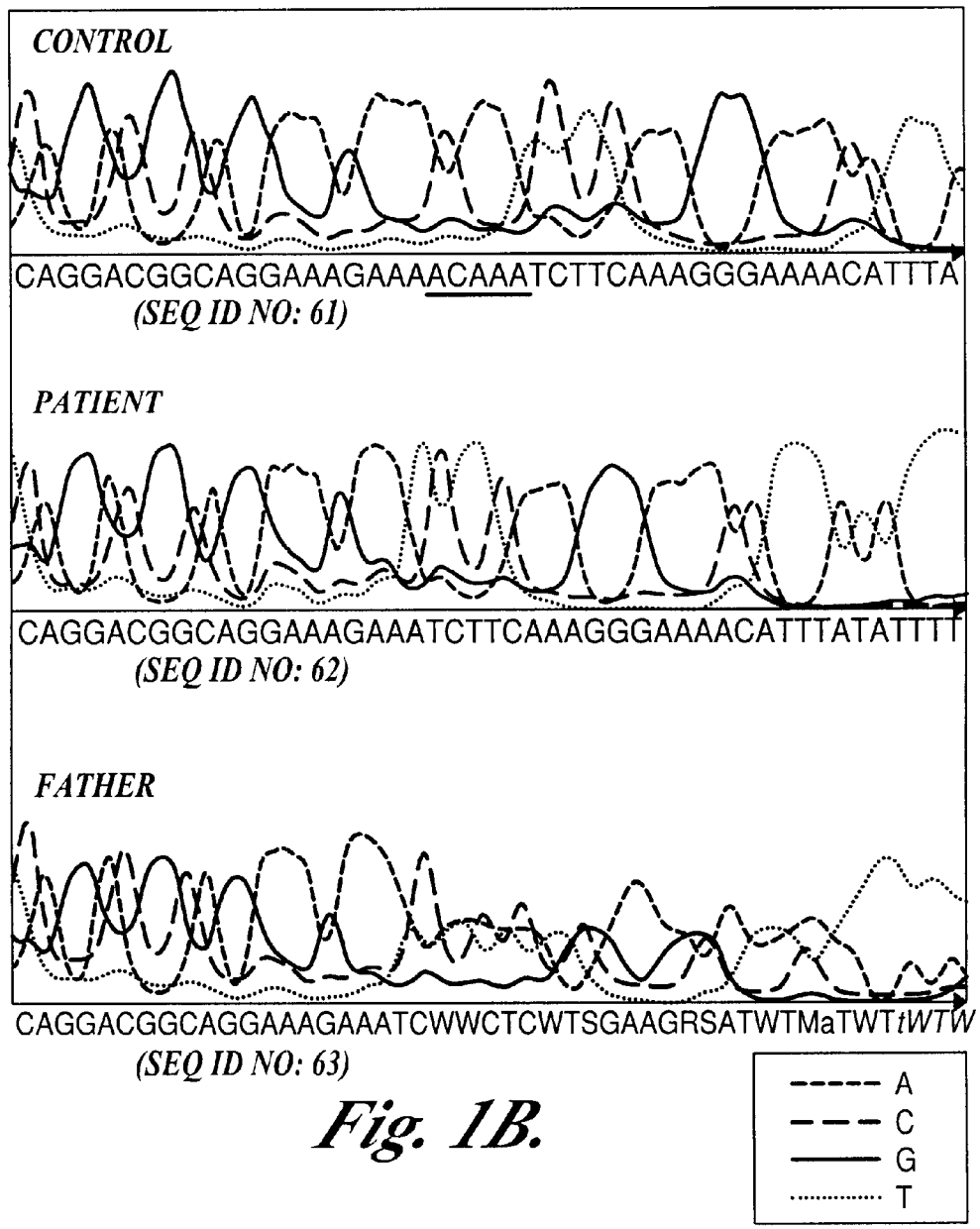

FIGS. 1A and 1B: Detection of the common 657del5 mutation of probable Slavic origin. 1A: SSCP pattern of exon 6 of Polish NBS family F24. 1B: Segment of genomic sequence of exon 6 in a control DNA, the patient, and the father from family F24. The five bp deleted in the patient are marked with a bar in the control sequence. In the sequence of the heterozygote father, a frameshift in the sequence starting at the deletion site can be seen.

FIGS. 2A–D: NBS1 nucleotide sequence (SEQ ID NO:1) and nibrin amino acid sequence (SEQ ID NO:2). The following designation are used: Underlined: mutation 657del5; hatched boxes: exons with odd numbers; bold (residues 24–100): FHA domain; bold/italic (residues 108–195): BRCT domain; italic (nucleotides 3853–4384): L1MC/D genome wide repeat; underlined and dashed boxes: polyadenylation signal & site.

Figure 3:
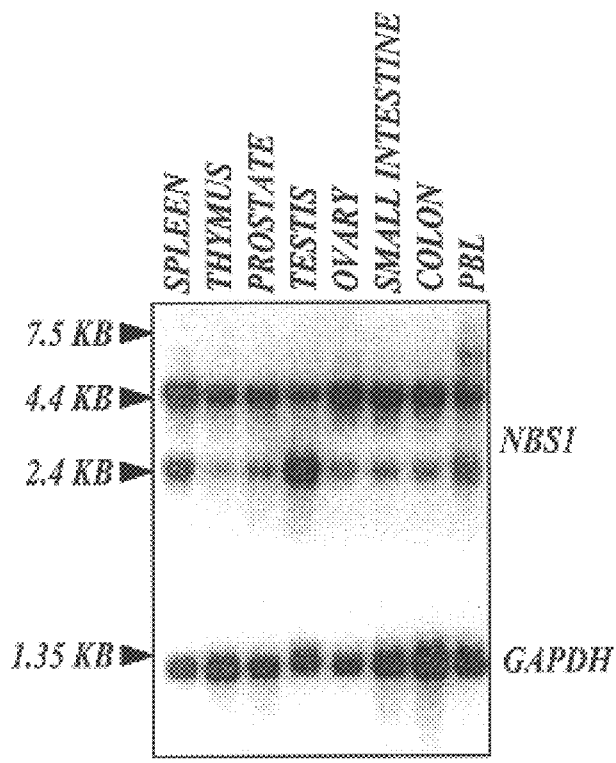

FIG. 3: Expression of the NBS1 gene in multiple human tissues. A commercial multiple tissue Northern blot was sequentially hybridized with probes for NBS1 and GAPDH (as a control for loading). Tissue of origin for RNA is indicated above. Migration of size markers is indicated at left.

Figure 4A:
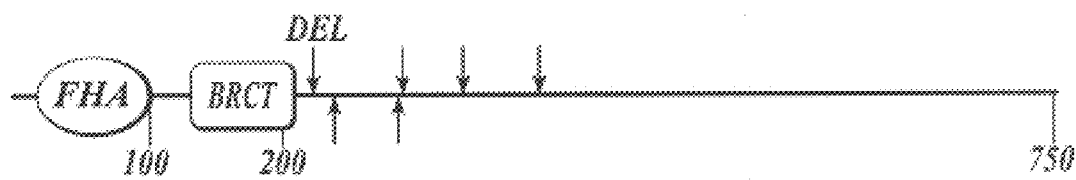
Figure 4C:
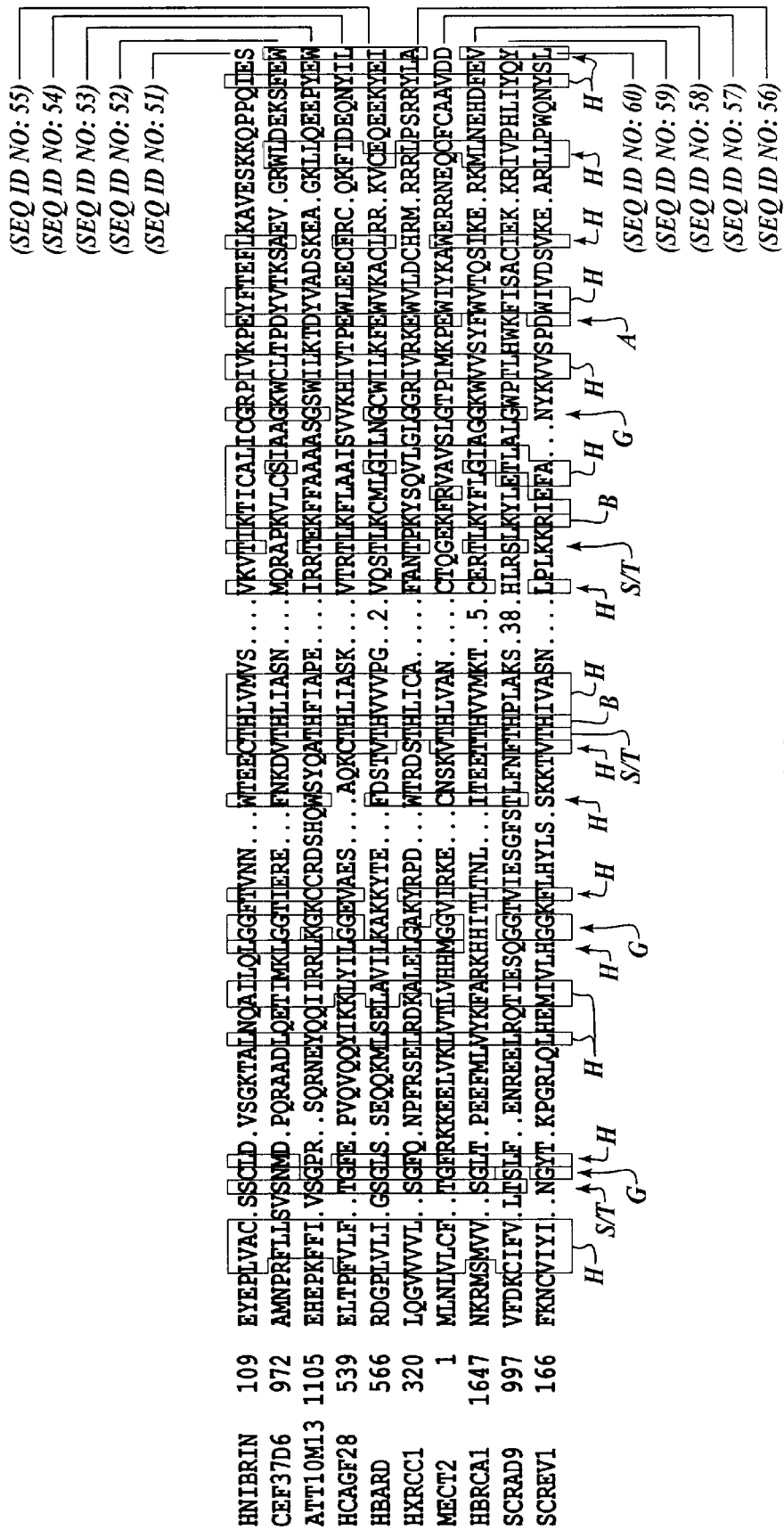

FIGS. 4A–4C: FHA and BRCT domains in nibrin. (4A) Localization of domains and of mutations (arrows) detected in patients with NBS. The common 5 bp deletion, 654del5, of Slavic origin is tagged ("DEL"). (4B), (4C) Multiple sequence alignments with known FHA and BRCT domains. Sequences are denoted by species identification prefixes (h, human; m, mouse; At, *A. thaliana*; Sc, *S. cerevisiae*; Sp, *S. pombe*; As, Anabaena Sp.; Ce, *C. elegans*) and by protein acronyms (the kinase-associated protein phosphatase KAPP; the forkhead and -like proteins FKH1 and FHL1; the protein kinases SPK1, DUN1 and MEK1, that all have been described to act in the nucleus and to respond to signals related to DNA replication and repair; the protein kinase CDS1 known to act in the S-phase checkpoint; the antigen K167, expressed in a cell-cycle dependent manner; the FRAH protein involved in differentiation from vegetative cells to heterocysts; conceptual translations of the cosmids F37D6.1 and T10M13.12; the CAG trinucleotide repeat containing cDNA CAGF28; the BRCA-associated RING finger domain protein BARD; the DNA repair proteins XRCC1 and REV1; the oncoprotein ECT2; the breast cancer susceptibility type 1 protein BRCA1; the radiation sensitive checkpoint protein RAD9. Numbers in the alignment denote amino acids omitted from the alignment. The following symbols are used: H indicates hydrophobic amino acids; G indicates glycine; B indicates basic amino acids; A indicates acidic amino acids; S/T indicates serine or threonine.

5. DETAILED DESCRIPTION OF THE INVENTION

Mutation screening of the NBS1 gene identified a number of distinct mutations in various NBS patients, summarized in Table 1. The vast majority of the patients are homozygous for the common deletion mutation 657del5, which is found exclusively on the conserved slavic haplotype. Three other mutations are deletions of 1 or 4 bp, and one was an insertion of a single nucleotide. All are predicted to cause a frameshift and thus premature truncation. One further mutation, 976C>T, is a point mutation creating a stop codon (Q326X) in exon 8 in a Dutch patient who is homozygous for this mutation. This collection of nonsense mutations in NBS patients represents compelling evidence that we have indeed identified the NBS gene. All such mutations occur downstream of the FHA and BRCT domains in nibrin. Various aspects of this gene and its mutations are described in detail in the sections below.

The identification of nibrin as the NBS1 gene product implies its role in the mammalian response to DNA double strand breaks. This is corroborated by the identification of protein domains which have been previously found in DNA damage-responsive cell-cycle checkpoint proteins. In the aminoterminal region, a forkhead associated domain (FHA) is present. This domain is possibly involved in mediating phospho-ser/thr-specific interactions and has been found in *S. cerevisiae* DUN1 and RAD53, two protein kinases linking the S-phase checkpoint to DNA-damage repair and in *S. pombe* cds1, a kinase acting in the S-phase checkpoint. The BReast cancer Carboxy-Terminal domain (BRCT) is found in a variety of diverse proteins whose unifying theme seems to be participation in DNA damage-responsive cell-cycle checkpoints.

5.1. THE NBS1 CODING SEQUENCE

The present invention relates to nucleic acid molecules that encode polypeptides referred to as nibrin. In a specific embodiment by way of example in Section 6, infra, full length human NBS1 nucleic acid molecules were cloned, and their nucleotide and deduced amino acid sequences characterized (SEQ ID NOS:1 and 2). Human NBS1 gene product, nibrin, contains 754 amino acids. In accordance with the invention, any nucleotide sequence which encodes the amino acid sequence of human NBS1 gene product can be used to generate recombinant molecules which direct the expression of the NBS1 gene. Additionally, the invention also relates to a fusion polynucleotide between an NBS1 coding sequence and a second coding sequence for a heterologous protein.

In order to clone full length homologous cDNA sequences from any species encoding the entire NBS1 cDNA or to clone family members or variant forms such as allelic variants, labeled DNA probes made from fragments corresponding to any part of the cDNA sequences disclosed herein may be used to screen a cDNA library. Examples of these sequences include those of SEQ ID NOS:3–40. More specifically, oligonucleotides corresponding to either the 5' or 3' terminus of the coding sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCl, pH 7.5, before being allowed to air dry. The filters are prehybridized in casein hybridization buffer containing 10% dextran sulfate, 0.5M NaCl, 50 mM Tris HCL, pH 7.5, 0.1% sodium pyrophosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained.

It may be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. To obtain the 5' end of the cDNA, PCR is carried out on 5'-RACE-Ready cDNA using the provided anchor primer and the 3' primer. A secondary PCR is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, a forkhead-associated domain and a breast cancer carboxyl-terminal domain, and finally overall structural similarity to the NBS1 gene disclosed herein.

Alternatively, a labeled probe may be used to screen a genomic library derived from any organism of interest using appropriate stringent conditions as described, infra.

Isolation of a NBS1 coding sequence or a homologous sequence may be carried out by the polymerase chain reactions (PCR) using two degenerate oligonucleotide primer pools designed on the basis of the NBS1 coding sequences disclosed herein. The template for the reaction may be cDNA obtained by reverse transcription (RT) of mRNA prepared from, for example, human or non-human cell lines or tissues known or suspected to express a NBS1 gene allele.

The PCR product may be subcloned and sequenced to ensure that the amplified sequences represent the sequence of a NBS1 coding sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source. A RT reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated.

A cDNA clone of a mutant or allelic variant of the NBS1 gene may be isolated, for example, by using PCR. In this case, the first cDNA strand may be synthesized by hybridizing an oligo-dT oligonucleotide to mRNA isolated from tissue known or suspected to be expressed in an individual putatively carrying the mutant NBS1 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant NBS1 allele to that of the normal NBS1 allele, the mutation(s) responsible for the loss or alteration of function of the mutant NBS1 gene product can be ascertained.

Alternatively, a genomic library can be constructed using DNA obtained from an individual suspected of or known to carry a mutant NBS1 allele, or a cDNA library can be constructed using RNA from a tissue known, or suspected, to express a mutant NBS1 allele. An unimpaired NBS1 gene or any suitable fragment thereof may then be labeled and used as a probe to identify the corresponding mutant NBS1 allele in such libraries. Clones containing the mutant NBS1 gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant NBS1 allele in an individual suspected of or known to carry such a mutant allele. In this manner, gene products made by the putatively mutant tissue may be expressed and screened using standard antibody screening techniques in conjunction with antibodies raised against the normal NBS1 gene product, as described, below, in Section 5.4. (For screening techniques, see, for example, Harlow and Lane, eds., 1988, "Antibodies: A Laboratory Manual", Cold Spring Harbor Press, Cold Spring Harbor.)

In cases where a NBS1 mutation results in an expressed gene product with altered function (e.g., as a result of a missense), a polyclonal set of anti-NBS1 gene product antibodies are likely to cross-react with the mutant NBS1 gene product. Library clones detected via their reaction with such labeled antibodies can be purified and subjected to sequence analysis according to methods well known to those of skill in the art.

The invention also relates to isolated or purified polynucleotides having at least 12 nucleotides (i.e., a hybridizable portion) of a NBS1 coding sequence or its complement. In other embodiments, the polynucleotides contain at least 25 (continuous) nucleotides, 50 nucleotides, 100 nucleotides, 150 nucleotides, or 200 nucleotides of a NBS1 coding sequence, or a full-length NBS1 coding sequence. Nucleic acids can be single or double stranded. Additionally, the invention relates to polynucleotides that selectively hybridize to a complement of the foregoing coding sequences. In preferred embodiments, the polynucleotides contain at least 12, 25, 50, 100, 150 or 200 nucleotides or the entire length of a NBS1 coding sequence.

In a specific embodiment, a polynucleotide which hybridizes to a NBS1 coding sequence (e.g., having sequence SEQ ID NO:1) or its complement under conditions of low stringency is provided. By way of example and not limitation, exemplary conditions of low stringency are as follows (Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

In another specific embodiment, a polynucleotide which hybridizes to a NBS1 coding sequence or its complement under conditions of high stringency is provided. By way of example and not limitation, exemplary conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100. µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a polynucleotide which hybridizes to a NBS1 coding sequence or its complement under conditions of moderate stringency is provided. Exemplary conditions of moderate stringency are as follows: Filters containing DNA are pretreated for 6 h at 55° C. in a solution containing 6×SSC, 5×Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art.

5.2. THE NIBRIN POLYPEPTIDES

In accordance with the invention, a NBS1 polynucleotide which encodes full length nibrin polypeptides, mutant polypeptides, peptide fragments of nibrin, nibrin fusion proteins or functional equivalents thereof, may be used to generate recombinant DNA molecules that direct the expression of nibrin polypeptides, mutant polypeptides, nibrin peptide fragments, nibrin fusion proteins or a functional equivalent thereof, in appropriate host cells. Such polynucleotides, as well as other polynucleotides which selectively hybridize to at least a part of such NBS1 polynucleotides or their complements, may also be used to produce nibrin polypeptides or in nucleic acid hybridization assays, such as Southern and Northern blot analyses, etc. The polypeptide products encoded by such polynucleotides may be naturally occurring or altered by molecular manipulation of the coding sequence.

Due to the inherent degeneracy of the genetic code, other DNA sequences which encode substantially the same or a functionally equivalent nibrin amino acid sequence (SEQ ID NO:2), may be used in the practice of the invention for the cloning and expression of nibrin proteins. Such DNA sequences include those which are capable of hybridizing to the human NBS1 coding sequence or its complementary sequence under low, moderate or high stringency conditions as described in Section 5.1, supra.

Altered nucleotide sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within its sequence, which result in a silent change thus producing a functionally equivalent nibrin protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine and tyrosine; and amino acids with nonpolar head groups include alanine, valine, isoleucine, leucine, phenylalanine, proline, methionine and tryptophan.

The nucleotide sequences of the invention may be engineered in order to alter a NBS1 coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc. Alterations may also affect one or more biologic activities of nibrin. For example, cysteine residues can be deleted or substituted with another amino acid to eliminate disulfide bridges.

Based on the domain organization of nibrin, nibrin mutant polypeptides can be constructed by rearranging the nucleotide sequences that encode the nibrin domains. For example, mutant polypeptides containing a forkhead-associated domain or a breast cancer carboxy-terminal domain can be generated.

In another embodiment of the invention, a NBS1 coding sequence, a modified NBS1 sequence or a truncated NBS1 coding sequence corresponding to a specific domain may be ligated to a heterologous sequence to produce a fusion protein. For example, for screening of peptide libraries for molecules that bind nibrin, it may be useful to encode a chimeric nibrin protein expressing a heterologous epitope that is recognized by a commercially available antibody. A fusion protein may also be engineered to contain a cleavage site located between a nibrin sequence and the heterologous protein sequence, so that the nibrin may be cleaved and separated from the heterologous moiety.

In a specific embodiment of the invention, the coding sequence of NBS1 could be synthesized in whole or in part, using chemical methods well known in the art. See, for example, Caruthers el al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letter* 21:719; and Chow and Kempe, 1981, *Nuc. Acids Res.* 9(12):2807–2817. Alternatively, the polypeptide itself could be produced using chemical methods to synthesize an nibrin amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles*, W.H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles*, W.H. Freeman and Co., N.Y., pp. 34–49).

In a specific embodiment-of the invention, a polypeptide containing at least 10 (continuous) amino acids of the nibrin protein is provided. In other embodiments, the polypeptide may contain at least 20 or 50 amino acids. In specific embodiments, such polypeptides do not contain more than 100, 150 or 200 amino acids. Derivatives or analogs of the polypeptides include, but are not limited to, molecules containing regions that are substantially homologous to the nibrin protein or fragments thereof (e.g., in various embodiments, at least 60% or 70% or 80% or 90% or 95% identity over an amino acid sequence of identical size or when compared to an aligned sequence in which the alignment is done by a computer homology program known in the art) or product encoded by a polynucleotide that is capable of hybridizing to a naturally-occurring coding sequence, under highly stringent, moderately stringent, or low stringent conditions.

The derivatives and analogs of nibrin protein can be produced by various methods known in the art. The manipulations which result in their production can occur at the nucleic acid or protein level. For example, a cloned coding sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of a polynucleotide encoding a derivative or analog, care should be taken to ensure that the modified coding sequence remains within the same translational reading frame as nibrin, uninterrupted by translational stop signals, in the coding region where the functional domain is encoded.

Additionally, the coding sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:655 1), use of TAB® linkers (Pharmacia), and the like.

Manipulations may also be made at the protein level. Included within the scope of the invention are protein fragments or other derivatives or analogs which are differentially modified during or after translation, e.g., by glycosylation, acetylation, phosphorylation, amidation, derivatization by known protecting/blocking groups, proteolytic cleavage, linkage to a heterologous polypeptide or another protein domain. Any of numerous chemical modifications may be carried out by known techniques, including but not limited to, specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives can be chemically synthesized. Nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ϵ-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the derivative is a chimeric or fusion protein containing nibrin or a fragment thereof joined at its amino- or carboxy-terminus to a heterologous protein via a peptide bond. Alternatively, the proteins are connected by a flexible polylinker such as Gly-Cys-Gly or Gly-Gly-Gly-Gly-Ser (SEQ ID NO: 64) repeated 1 to 3 times (Bird et al., 1988, Science 242:423–426; Chaudhary et al., 1990, Proc. Nat'l. Acad. Sci. U.S.A. 87:1066–1070). In one embodiment, such a chimeric protein is produced by recombinant expression of a nucleic acid encoding the protein (a NBS1 coding sequence joined in-frame to a coding sequence for another antigen or a heterologous protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of the NBS1 coding sequence fused to any other coding sequences may be constructed.

In another specific embodiment, the derivative is a molecule comprising a region of homology with nibrin. By way of example, in various embodiments, a protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art.

5.3. PRODUCTION OF NIBRIN POLYPEPTIDES

In order to produce a biologically active nibrin, the nucleotide sequence coding for nibrin, or a functional equivalent, is inserted into an appropriate expression vector, i.e., a vector which contains the necessary elements for the transcription and translation of the inserted coding sequence. The NBS1 gene product as well as host cells or cell lines transfected or transformed with recombinant NBS1 gene-containing expression vectors can be used for a variety of purposes. These include, but are not limited to, large scale production of nibrin protein, use of nibrin as immunogen for antibody generation and screening of compounds that bind nibrin.

Methods which are well known to those skilled in the art can be used to construct expression vectors containing the NBS1 coding sequence and appropriate transcriptional/translational control signals. These methods include in vitro recombinant DNA techniques, synthetic techniques and in vivo recombination/genetic recombination. (See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). RNA capable of encoding nibrin polypeptide may also be chemically synthesized (Gait, ed., 1984, Oligonucleotide Synthesis, IRL Press, Oxford).

A variety of host-expression vector systems may be utilized to express the NBS1 coding sequence. These include, but are not limited to, microorganisms such as bacteria (e.g., E. coli, B. sublilis) transformed with recombinant bacteriophage DNA, plasmid DNA or cosmid DNA expression vectors containing the NBS1 coding sequence; yeast (e.g., Saccharomyces, Pichia) transformed with recombinant yeast expression vectors containing the NBS1 coding sequence; insect cell systems infected with recombinant virus expression vectors (e.g., baculovirus) containing the NBS1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the NBS1 coding sequence; or mammalian cell systems (e.g., COS, CHO, BHK, 293, 3T3 cells). The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the NBS1 coding sequence, SV40-, BPV- and EBV-based-vectors may be used with an appropriate selectable marker.

5.3.1. EXPRESSION SYSTEMS

In bacterial systems a number of expression vectors may be advantageously selected depending upon the use intended for the expressed NBS1 gene product. For example, when large quantities of nibrin protein are to be produced for the generation of antibodies, screening peptide libraries or formulating pharmaceutical compositions, vectors which direct the expression of high levels of fusion protein products that are readily purified may be desirable. Such vectors include but are not limited to the E. coli expression vector pUR278 (Ruther et al., 1983, EMBO J. 2:1791), in which the NBS1 coding sequence may be ligated into the vector in frame with the lacZ coding region so that a hybrid protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used (Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. 11, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathem et al., Cold Spring Harbor Press, Vols. I and II).

In cases where plant expression vectors are used, the expression of the NBS1 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, ep, soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. (Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9).

An alternative expression system which could be used to express NBS1 is an insect system. In one such system, Autographa californica nuclear polyhedrosis virus (AcNPV) is used as a vector to express foreign genes. The virus grows in Spodoptera frugiperda cells. The NBS1 coding sequence may be cloned into non-essential regions (for example the polyhedron gene) of the virus and placed under control of an AcNPV promoter (for example the polyhedron promoter). Successful insertion of the NBS1 coding sequence will result in inactivation of the polyhedron gene and production of non-occluded recombinant virus (i.e., virus lacking the proteinaceous coat coded for by the polyhedron gene). These recombinant viruses are then used to infect Spodoptera frugiperda cells in which the inserted gene is expressed (e.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the NBS1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing NBS1 in infected hosts (e.g., See Logan & Shenk, 1984, Proc. Natl. Acad. Sci. USA 81:3655–3659). Alternatively, the vaccinia 7.5K promoter may be used (See, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931). Regulatable expression vectors such as the tetracycline repressible vectors may also be used to express the coding sequences in a controlled fashion.

Specific initiation signals may also be required for efficient translation of inserted NBS1 coding sequences. These signals include the ATG initiation codon and adjacent sequences. In cases where the entire NBS1 gene, including its own initiation codon and adjacent sequences, is inserted into the appropriate expression vector, no additional translational control signals may be needed. However, in cases where only a portion of the NBS1 coding sequence is inserted, exogenous translational control signals, including the ATG initiation codon, must be provided. Furthermore, the initiation codon must be in phase with the reading frame of the NBS1 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, W138, etc.

For long-term, high-yield production of recombinant proteins, stable expression is preferred. For example, cell lines which stably express the nibrin protein may be engineered. Rather than using expression vectors which contain viral origins of replication, host cells can be transformed with the NBS1 coding sequence controlled by appropriate expression control elements (e.g., promoter and/or enhancer sequences, transcription terminators, polyadenylation sites, etc.), and a selectable marker. Following the introduction of foreign DNA, genetically engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the nibrin protein. Such engineered cell lines are particularly useful in screening for molecules or drugs that affect nibrin function.

A number of selection systems may be used, including but not limited to, the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Proc. Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Additional selectable genes include trpB, which allows cells to utilize indole in place of tryptophan; hisD, which allows cells to utilize histinol in place of histidine (Hartman & Mulligan, 1988, Proc. Natl. Acad. Sci. USA 85:8047); ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.) and glutamine synthetase (Bebbington et al., 1992, Biotech 10:169).

The expression characteristics of an endogenous NBS1 gene within a cell line or microorganism may be modified by inserting a heterologous DNA regulatory element into the genome of a stable cell line or cloned microorganism such that the inserted regulatory element is operatively linked with the endogenous NBS1 gene. For example, an endogenous NBS1 gene which is normally "transcriptionally silent", i.e., an NBS1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous NBS1 gene may be activated by insertion of a promiscuous regulatory element that works across cell types.

A heterologous regulatory element may be inserted into a stable cell line or cloned microorganism, such that it is operatively linked with an endogenous NBS1 gene, using techniques, such as targeted homologous recombination, which are well known to those of skill in the art (e.g., in Chappel, U.S. Pat. No. 5,272,071; PCT publication No. WO 91/06667, published May 16, 1991).

5.3.2. PROTEIN PURIFICATION

Once a recombinant protein is expressed, it can be identified by assays based on the physical or functional properties of the product, including radioactive labeling of the product followed by analysis by gel electrophoresis, radioimmunoassay, ELISA, bioassays, etc.

Once the encoded protein is identified, it may be isolated and purified by standard methods including chromatography (e.g., high performance liquid chromatography, ion exchange, affinity, and sizing column chromatography), centrifugation, differential solubility, or by any other standard technique for the purification of proteins. The actual conditions used will depend, in part, on factors such as net charge, hydrophobicity, hydrophilicity, etc., and will be apparent to those having skill in the art. The functional properties may be evaluated using any suitable assay such as lipase activities. For the practice of the present invention, it is preferred that the polypeptide is at least 80% purified from other proteins. It is more preferred that they are at least 90% purified.

In another alternate embodiment, native proteins can be purified from natural sources, by standard methods such as those described above (e.g., immunoaffinity purification). In a specific embodiment of the present invention, the nibrin polypeptides, whether produced by recombinant DNA techniques or by chemical synthetic methods or by purification from natural sources include, but are not limited to, those containing, as a primary amino acid sequence, all or part of the amino acid sequences substantially as recited in SEQ ID NO:2, as well as fragments and other derivatives, and analogs thereof, including proteins homologous thereto.

5.4. IDENTIFICATION OF CELLS THAT EXPRESS NIBRIN

The host cells which contain the coding sequence and which express an NBS1 gene product, fragments thereof, or an nibrin fusion protein may be identified by at least four general approaches; (a) DNA—DNA or DNA-RNA hybridization; (b) the presence or absence of "marker" gene functions; (c) assessing the level of transcription as measured by the expression of NBS1 mRNA transcripts in the host cell; and (d) detection of the gene product as measured by immunoassay or by its biological activity. Prior to the identification of gene expression, the host cells may be first mutagenized in an effort to increase the level of expression of NBS1, especially in cell lines that produce low amounts of NBS1.

In the first approach, the presence of the NBS1 coding sequence inserted in the expression vector can be detected by DNA—DNA or DNA-RNA hybridization using probes comprising nucleotide sequences that are homologous to the NBS1 coding sequence or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the NBS1 coding sequence is inserted within a marker gene sequence of the vector, recombinants containing the NBS1 coding sequence can be identified by the absence of the marker gene function. Alternatively, a marker gene can be placed in tandem with the NBS1 coding sequence under the control of the same or different promoter used to control the expression of the NBS1 coding sequence. Expression of the marker in response to induction or selection indicates expression of the NBS1 coding sequence.

In the third approach, transcriptional activity for the NBS1 coding region can be assessed by hybridization assays. For example, RNA can be isolated and analyzed by Northern blot using a probe homologous to the NBS1 coding sequence or particular portions thereof. Alternatively, total nucleic acids of the host cell may be extracted and assayed for hybridization to such probes. Additionally, RT-PCR may be used to detect low levels of gene expression.

In the fourth approach, the expression of the nibrin protein can be assessed immunologically, for example by-Western blots, immunoassays such as radioimmuno-precipitation, enzyme-linked immunoassays and the like. This can be achieved by using an anti-nibrin antibody. Alternatively, the ability of nibrin to prevent DNA double strand breaks can be determined in appropriate bioassays.

5.5. ANTIBODIES TO NIBRIN

Antibodies directed to nibrin are useful for the identification and isolation of nibrin. In a preferred embodiment, an anti-nibrin antibody competitively inhibits nibrin function and neutralizes its activity. Anti-nibrin antibodies may be used in detecting and quantifying expression of nibrin levels in cells and tissues.

Various procedures known in the art may be used for the production of antibodies to epitopes of the naturally-occurring, synthetic and recombinantly produced nibrin protein. Such antibodies include, but are not limited to, polyclonal, monoclonal, chimeric, humanized, single chain, anti-idiotypic, antigen-binding antibody fragments and fragments produced by a variable region expression library.

For the production of antibodies, various host animals may be immunized by injection with the recombinant or naturally purified nibrin protein, fusion protein or peptides, including but not limited to rabbits, mice, rats, hamsters, and the like. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum.*

Monoclonal antibodies to nibrin may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). Such antibodies may be of any immunoglobulin class including, but not limited to, IgG, IgM, IgE, IgA, IgD and any subclass thereof. The hybridoma producing the monoclonal antibodies of this invention may be cultivated in vitro or in vivo.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454; U.S. Pat. Nos. 4,816,567 and 4,816,397) by splicing the genes from a mouse antibody molecule of appropriate antigen specificity together with genes from a human antibody molecule of appropriate biological activity can be used. Humanized antibodies may be generated according to the methods described in U.S. Pat. Nos. 5,693,762; 5,585,089 and 5,565,332.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against gene products of interest. Single chain antibodies are formed by linking the heavy and light chain fragments of the Fv region via an amino acid bridge, resulting in a single chain polypeptide.

Antibodies to the polypeptides of the invention can, in turn, be utilized to generate anti-idiotype antibodies that mimic an epitope of the polypeptide of interest, using techniques well known to those skilled in the art. (See, e.g., Greenspan & Bona, 1993, FASEB J 7(5):437–444; and Nissinoff, 1991, J. Immunol. 147(8):2429–2438). For example, antibodies which competitively inhibit the binding of an antibody to an antigenic peptide may mimic the antigenic epitope of the peptide. Such neutralizing anti-idiotypes or Fab fragments of such anti-idiotypes can be used.

Hybridomas may be screened using enzyme-linked innunosorbent assays (ELISA) or radioimmunoassays in order to detect cultures secreting antibodies specific for refolded recombinant nibrin. Subsequent testing may use recombinant nibrin fragments to identify the specific portion of the nibrin molecule with which a monoclonal antibody binds. Additional testing may be used to identify monoclonal antibodies with desired functional characteristics such as staining of histological sections, immunoprecipitation or Western blotting of nibrin, or neutralization of nibrin activity. Determination of the monoclonal antibody isotype may be accomplished by ELISA, thus providing additional information concerning purification or function.

Antibody fragments which recognize specific binding sites of nibrin may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281; U.S. Pat. Nos. 5,223,409; 5,403,484 and 5,571,698) to allow rapid and easy identification of monoclonal Fab fragments with the desired specificity to nibrin. Antibody constant regions can be altered by molecular manipulations to modify their effector functions (U.S. Pat. No. 5,624,82 1). The complementarity-determining regions (CDR) of an antibody can be identified, and synthetic peptides corresponding to such regions are used to mediate antigen binding (U.S. Pat. No. 5,637,677).

5.6. USES OF GENETICALLY ENGINEERED HOST CELLS

In an embodiment of the invention, the nibrin protein and/or cell lines that express nibrin may be used to screen for antibodies, peptides, small molecules, natural and synthetic compounds or other cell bound or soluble molecules that bind to the nibrin protein. For example, anti-nibrin antibodies may be used detect its preserice. Alternatively, screening of peptide libraries with recombinantly expressed soluble nibrin protein or cell lines expressing nibrin protein may be useful for identification of therapeutic molecules that function by inhibiting or stimulating the biological activities of nibrin.

Random peptide libraries consisting of all possible combinations of amino acids attached to a solid phase support may be used to identify peptides that are able to bind to nibrin (Lam, K. S. et al., 1991, Nature 354: 82–84). The screening of peptide libraries may have therapeutic value in the discovery of pharmaceutical agents that stimulate or inhibit the biological activities of nibrin.

Identification of molecules that are able to bind to the nibrin protein may be accomplished by screening a peptide library with recombinant soluble nibrin protein. Methods for expression and purification of nibrin are described in Section 5.3, supra, and may be used to express recombinant full length nibrin or fragments of nibrin depending on the functional domains of interest.

To identify and isolate the peptide/solid phase support that interacts and forms a complex with nibrin, it may be necessary to label or "tag" the nibrin molecule. In addition, anti-nibrin antibody may be used to detect nibrin bound to a second molecule. The nibrin protein may be conjugated to enzymes such as alkaline phosphatase or horseradish peroxidase or to other reagents such as fluorescent labels which may include fluorescein isothiocyanate (FITC), phycoerythrin (PE) or rhodamine. Conjugation of any given label to nibrin may be performed using techniques that are well known in the art. Alternatively, NBS1-containing expression vectors may be engineered to express a chimeric nibrin protein containing an epitope for which a commercially available antibody exist. The epitope specific antibody may be tagged using methods well known in the art including labeling with enzymes, fluorescent dyes or colored or magnetic beads.

The "tagged" nibrin conjugate is incubated with the random peptide library for 30 minutes to one hour at 22° C. to allow complex formation between nibrin and peptide species within the library. The library is then washed to remove any unbound protein. If nibrin has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3,3',4,4"-diaminobenzidine (DAB), respectively. After incubating for several minutes, the peptide/solid phase-nibrin complex changes color, and can be easily identified and isolated physically under a dissecting microscope with a micromanipulator. If a fluorescent tagged nibrin molecule has been used, complexes may be isolated by fluorescence activated sorting. If a chimeric nibrin protein expressing a heterologous epitope has been used, detection of the peptide/nibrin complex may be accomplished by using a labeled epitope specific antibody. Once isolated, the identity of the peptide attached to the solid phase support may be determined by peptide sequencing.

5.7. USES OF NBS1 POLYNUCLEOTIDE

5.7.1. DIAGNOSTIC USES

The cloning and characterization of the NBS1 gene provides the first evidence for a gene associated with NBS in patients. A NBS1 polynucleotide may be used for diagnostic and/or therapeutic purposes. For diagnostic purposes, a NBS1 polynucleotide may be used to detect the level of NBS1 gene expression, aberrant NBS1 gene expression, mutations or polymorphisms associated with disease states.

In another aspect, the oligonucleotide primers may be constructed from regions of the polynucleotide of the invention. By using two or more of such primers, for example, one may detect the presence of polynucleotide sequences specific for NBS mutations in a biological sample using, for example, the PCR.

In yet another aspect, oligonucleotides may be used in an oligonucleotide ligation assay ("OLA") to detect NBS1 in a biological sample. Alternatively, such an OLA assay may be used to detect a mutation in NBS1.

5.7.2. THERAPEUTIC USES

A NBS1 polynucleotide may be useful in the treatment of NBS. By introducing gene sequences into cells, gene therapy can be used to treat conditions in which the cells do not express normal NBS1 or express abnormal/inactive NBS1. In some instances, the polynucleotide encoding NBS1 is intended to replace or act in the place of a functionally deficient endogenous gene. Alternatively, abnormal conditions characterized by overexpression can be treated using the gene therapy techniques described below.

In a specific embodiment, nucleic acids comprising a sequence encoding nibrin or a functional derivative thereof, are administered to promote NBS1 function, by way of gene therapy. Gene therapy refers to therapy performed by the administration of a nucleic acid to a subject. In this embodiment of the invention, the nucleic acid produces its encoded protein that mediates a therapeutic effect by promoting nibrin function. Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred embodiment of the invention, the therapeutic composition comprises an NBS1 coding sequence that is part of an expression vector. In particular, such a nucleic acid has a promoter operably linked to the NBS1 coding sequence, said promoter being inducible or constitutive, and, optionally, tissue-specific. In another specific embodiment, a nucleic acid molecule is used in which the NBS1 coding sequence and any other desired sequences are flanked by regions that promote homologous recombination at a desired site in the genome, thus providing for intrachromosomal expression of the NBS1 nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, Dupont), by coating with lipids or cell-surface receptors or transfecting agents, by encapsulation in liposomes, microparticles, or microcapsules, by administering it in linkage to a peptide which is known to enter the nucleus, or by administering it in linkage to a ligand subject to receptor-mediated endocytosis (see e.g., Wu and Wu, 1987, J. Biol. Chem. 262:4429–4432) which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a preferred embodiment of the invention, adenoviruses as viral vectors can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells (Kozarsky and Wilson, 1993, Current Opinion in Genetics and Development 3:499–503). Bout et al., (1994, Human Gene Therapy 5:3–10) demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234. Adeno-associated virus (AAV) has also been proposed for use in gene therapy (Walsh et al., 1993, Proc. Soc. Exp. Biol. Med. 204:289–300).

In addition, retroviral vectors (see Miller et al., 1993, Meth. Enzymol. 217:581–599) have been modified to delete retroviral sequences that are not necessary for packaging of the viral genome and integration into host cell DNA. The NBS1 coding sequence to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 30 3:110–114.

Another approach to gene therapy involves transferring a gene to cells in tissue culture. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, lipofection, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

6. EXAMPLE

Identification of NBS1 Gene and its Mutations in Nijmegen Breakage Syndrome Patients 6.1. MATERIALS AND METHODS 6.1.1. PATIENTS RNA AND DNA SAMPLES A total of 51 unrelated NBS families, mainly of Polish, but also Czech, German, Dutch, Italian, Mexican, Spanish, United Kingdom, Canadian and United States origin have been collected for this study. The diagnosis of NBS in all families was made as previously described (Saar et al., 1997, Am. J. Hum. Genet. 60:605–610). Blood samples were obtained from the families under informed consent. DNA was extracted from whole blood, using a Nucleon II Kit (Scotlab), according to the manufacturer's instructions. Total RNA was extracted from lymphoblastoid cell lines that had been established from 14 NBS patients using the phenol-chloroform procedure (Trizol, Life Technologies).

6.1.2. HAPLOTYPE ANALYSIS

Microsatellite markers from the interval D8S271–D8S270 on chromosome 8q21, namely AFM289zb5, D8S88 and D8S 1724, were analyzed as previously described (Saar et al., 1997, Am. J. Hum. Genet. 60:605–610) using primer sequences deposited in GDB. Newly ascertained microsatellites based on the genomic sequence derived from the BAC/PAC contig were designated H3GT, H2CA, H3GTA, H4CA and H5CA and amplified using standard conditions—5 min 94° C., 30 cycles (30s 94° C., 30s 55° C., 30s 72° C.) 7 min 72° C. Single nucleotide polymorphisms (SNPs) were amplified under the same conditions and detected through SSCP analysis as described in Section 6.1.6. infra.

The order of markers previously described in YAC contig WC8.8 of the Whitehead Institute (Hudson et al., 1995, Science 270:1945–1954) was verified through amplification from the three most relevant YACs 829G6, 820C9 and 952E8. We considered as true ancestral recombination events only those where the departure from the common haplotype was in at least in two adjacent microsatellites or a single nucleotide polymorphisms (SNPs). Variations of a single repeat unit from the common allele in isolated microsatellites, as is the case in haplotypes "F2F" and "F14M", were interpreted as ancestral mutational events in that microsatellite.

6.1.3. BAC CONTIG

DNA pools from a human BAC library (Research Genetics, Hunstville, Ala.) were screened by PCR, as described above, for the microsatellite markers D8S88, AFMzb289, D8S181 1 and D8S1724, and for ESTs previously assigned to this region (Schuler et al., 1996, Science 274:540–546)—A006J10, A005L21, WI-8975 (CALB) and stG9973 (DECR). Primers corresponding to these ESTs and PCR conditions were available on the World Wide Web site at http://www.ncbi.nlm.nih.gov/SCIENCE96/. A human PAC library (Genome Systems, Inc.) was also screened for the ESTs st69973 and A006J10.

BAC and PAC clone DNA was extracted using Qiagen Plasmid Midi Kit, as recommended by the manufacturer. BAC and PACs were sized and restriction mapped by digestion with NotI, SalI, BssHII and MluI (New England Biolabs), followed by Pulse-Field-Gel-Electrophoresis (PFGE) on a Rotaphor Type 5 apparatus (Biometra). BAC and PACs ends were sequenced with T7 and Sp6 primers using Cycle Sequencing Kit (Pharmacia) on an automated DNA Sequencer (ALF, Pharmacia).

6.1.4. FLUORESCENCE IN SITU HYBRIDIZATION (FISH)

Chromosome preparations were obtained from phytohemagglutinin-stimulated blood cell cultures by standard harvesting procedures. Isolated BAC-DNA was labeled with Cy3-dCTP (Amersham) by standard nick translation procedure (GibcoBRL Nick Translation System). The labeled DNA-samples (1 µg) were ethanol precipitated with sonicated herring sperm DNA (10 µg), Cot-1 DNA (10 µg) and dissolved in 40 µl hybridization mixture (50% deionized formamide, 2xSSC, 10% dextran sulfate). Chromosomal in situ suppression (CISS) hybridization was performed following standard protocols (Lichter and Cremer, 1992). Signal detection and imaging were achieved using a LEICA DMRB/E photomicroscope and the Cytovision system (Applied Imaging).

6.1.5. TRANSCRIPT DETECTION

Primers for ESTs previously reported to map to the interval D8S273–D8S270 and D8S270 D8S257 (Schuler et al., 1996, Science 274:540–546) were obtained from Research Genetics. All ESTs were typed on the BAC/PAC contig and on YACs 829G6, 820C9 and 952E8 (Hudson et al., 1995, Science 270:1945–1954) by PCR amplification as described above. Clones for ESTs mapped to the region were obtained from the German resource center (RZPD) and were entirely sequenced as described.

6.1.6. MUTATION DETECTION

First strand CDNA was synthesized from 1–2 µg total RNA with MMLV reverse transcriptase and random hexamer primers (Life Technologies) in a final volume of 20 µl (10 min 20° C., 40 min 42° C., 6 min 98° C.). 3 µl of this product was used for PCR-amplification. Specific primers for all transcripts were designed and overlapping cDNA fragments, suitable for SSCP analysis were amplified. When genomic sequences were available for a given transcript, genomic DNA of NBS patients was also amplified, using exon flanking primers. For all amplified fragments, SSCP analysis was performed (Orita et al., 1989, Genomics 5:874–879). Aliquots (3–5 µl) of PCR-products were mixed with an equal volume of loading buffer, denatured for 5 min at 95° C., chilled on ice and loaded on 12% non-denaturing polyacrylamide gels and electrophoresed under conditions as described (Savov et al., 1992, Nucl. Acids Res. 20:6741–6742). In parallel, samples from 2 controls and 2 parents were always run for comparison. The gels were scanned for aberrant migration after staining with Vistra Green on a FluorImager and the signals were analyzed with the ImagequaNT software (Molecular Dynamics). All samples which showed an aberrant SSCP shift were directly sequenced. After identification of the common mutation and the genomic organization of the NBS gene, flanking primers were designed for all 16 exons and the remaining NBS patients screened for mutations.

6.1.7. PRIMERS USED

Ex1 F 5'-TCATCCAAGGCAGCCTGCGT-3' (SEQ ID NO:3)
Ex1 R 5'-TGCCATACAGCGTACTCGCC-3' (SEQ ID NO:4)
Ex2 F 5'-CTTTGATAGCCTTCAGTGAG-3' (SEQ ID NO:5)
Ex2 R 5'-CTCTCTCTCACATACAAACC-3' (SEQ ID NO:6)
Ex3 F 5'-CAGTAATTGTTGTCTGCCGT-3' (SEQ ID NO:7)
Ex3 R 5'-AGGATTTGGCTGAAACAAAG-3' (SEQ ID NO:8)
Ex4 F 5'-GCTTAATGATGAGGAACTGA-3' (SEQ ID NO:9)
Ex4 R 5'-CCTAAATGGTATACAAAGGG-3' (SEQ ID NO:10)
Ex5 F 5'-TTATGGATGTAAACAGCCTC-3' (SEQ ID NO:11)
Ex5 R 5'-TACCGAACTATAACACAGCA-3' (SEQ ID NO:12)
Ex6 F 5'-CAGATAGTCACTCCGTTTACAA-3' (SEQ ID NO:13)
Ex6 R 5'-ATGAATAGGCCAGTTATCACAG-3' (SEQ ID NO:14)
Ex7 F 5'-TCAAGAAGTAGCACCAAGTC-3' (SEQ ID NO:15)
Ex7 R 5'-AATTGCTTGAACCCAGAAGG-3' (SEQ ID NO:16)
Ex8 F 5'-GAGGTTGCTTTATCTTGACA-3' (SEQ ID NO:17)
Ex8 R 5'-CCCTAGCAAGTATATAGATA-3' (SEQ ID NO:18)
Ex9 F 5'-CTTAGCATGGTATAGTCTAA-3' (SEQ ID NO:19)
Ex9 R 5'-CTCAAGAGACAACCTGATAA-3' (SEQ ID NO:20)
Ex10F 5'-TGCTTTCTTGGGATGGTAAA-3' (SEQ ID NO:21)

Ex10R 5'-GCAGAAGCATACTTAATCAG-3' (SEQ ID NO:22)
Ex11F 5'-ATGGTTACTTAGCTGTGTTC-3' (SEQ ID NO:23)
Ex11R 5'-TAATGGATGCTCATACTGTC-3' (SEQ ID NO:24)
Ex12F 5'-ATGCCTGGTCATACATAACA-3' (SEQ ID NO:25)
Ex12R 5'-AATTGATGAGATGACAGTCC-3' (SEQ ID NO:26)
Ex13F 5'-AGATTCCCAAATGACAAGTG-3' (SEQ ID NO:27)
Ex13R 5'-AGTTCATATCCTTCCTAGAG-3' (SEQ ID NO:28)
Ex14F 5'-AACATCTTTGGCACTTATGC-3' (SEQ ID NO:29)
Ex14R 5'-AGAAGAATTTGCTTGAAGGC-3' (SEQ ID NO:30)
Ex15F 5'-CTATTGGTTGTCTTTGAGTG-3' (SEQ ID NO:31)
Ex15R 5'-ATTTCACACAATTCGGGAAC-3' (SEQ ID NO:32)
Ex16a F 5'-TCATTCCCATCCTATTTGCC-3' (SEQ ID NO:33)
Ex16a R 5'-TGGAAGGGTGACTTTAGTCT-3' (SEQ ID NO:34)
Ex16b F 5'-AGGTAAAGACTAAAGTCACC-3' (SEQ ID NO:35)
Ex16b R 5'-TGTTTGATGAAGTCTCCACA-3' (SEQ ID NO:36)
Ex16c F 5'-AGTACTAGAAACTGAAGACC-3' (SEQ ID NO:37)
Ex16c R 5'-ATTTGGAAGGTGAGAGTGAT-3' (SEQ ID NO:38)
Ex16d F 5'-GTAAACAGAAGCAACAGAAG-3' (SEQ ID NO:39)
Ex16d R 5'-GGCAAGGTAATTTAATGAGG-3' (SEQ ID NO:40)

6.1.8. NORTHERN BLOT ANALYSIS

A probe containing nucleotides 704 to 1279 of the NBS1 gene (FIG. 2) was amplified from a cDNA clone, radio-labeled by incorporation of $[\alpha^{32}P]dCTP$ and $[\alpha^{32}P]dATP$ and hybridized overnight at 42° C. in 50% formamide to human multiple tissue poly-A+ northern blots (Clontech). The blots were washed 2 times for 20 minutes in 2×SSC/ 0.1% SDS at 42° C. and 1 time for 20 minutes in 0.2×SSC/ 0.1% SDS at 55° C. Blots were then stripped by washing in 0.01×SSC/0.01% SDS at 65° C. and hybridized with a radiolabelled GAPDH probe as a control for RNA loading.

6.1.9. NUCLEOTIDE SEQUENCING

The BACs and PACs were sequenced by the "shotgun method" as described previously (Platzer et al., 1997, Genome Res. 7:592–605). For low redundancy analysis ("skinmming") about 600 to 800 sequencing reads per 100 kb of human insert were obtained. In order to complete the sequence of selected clones, the number of reads was raised to about 2,500 per 100 kb.

6.1.10. COMPUTER ANALYSIS

Homology searches against databases were performed with BLAST (Version 1.4; Altschul et al., 1990, J. Mol. Biol. 215:403–410) and FASTA (Version 2.0; Pearson and Lipman, 1988, Proc. Natl. Acad. Sci. USA 85:2444–2448). Genome-wide repeats were identified with the REPEAT-MASKER program (A. F. A Smit and P. Green at http://ftp.genome.washington.edu/RM/RepeatMasker.html). FHA and BRCT domains in nibrin were identified using a new method for iterative database searches and construction of consensus strings (Beckmann et al., 1998, J. Mol. Biol. 275:725–730). Corroborative profile searches at ISREC's ProfileScan Server (http://ulrec3/unil.ch/software/profilescan.html) established statistical significance for the presence of the FHA domain, whereas the BRCT domain was cross-validated using MACAW (version 2.0.5; Schuler et al., 1991, Proteins 9:180–190).

6.2 RESULTS

6.2.1. FINE MAPPING THROUGH CONSERVED HAPLOTYPE ANALYSIS

A gene for NBS was previously mapped to a 1 cM region on chromosome 8q21 between markers D8S271 and D8S270 (Saar et al., 1997, Am. J. Hum. Genet. 60:605–610). Based on radiation hybrid data, this region was estimated to be as large as 8 Mb, too large for positional cloning. However, marked linkage disequilibrium was also observed between NBS and alleles at the microsatellite marker D8S1811 located within this minimal region and less strong linkage disequilibrium for the flanking markers D8S271 and D8S270. Therefore, other polymorphic markers were analyzed, which had been previously mapped to a YAC-contig of the region. All these markers also exhibited linkage disequilibrium, though they showed considerably more overlap in allelic distribution between normal and mutant chromosomes than D8S1811.

The full extent of the linkage disequilibrium only became apparent when haplotypes were constructed for these markers and compared them within the panel of 51 unrelated NBS patients, mostly of Polish or Czech origin. Five patients, of Italian, Mexican, English, Canadian and Dutch origin, exhibited at least one unique haplotype. The remaining patients shared a common haplotype across the entire interval from D8S271 to D8S270. Some patients only shared alleles at more central loci within this interval such as D8S1811 and D8S88, suggesting that ancestral recombination events had eroded the common haplotype. The NBS gene was believed to lie in the smallest segment oft he haplotype that was shared by all patients who exhibited at least part of the common ancestral haplotype.

To further refine the extent of the shared haplotype we identified and typed further polymorphisms from the region including microsatellites and SNPs detected in ESTs and cDNAs. Detailed haplotypes spanning the NBS critical region could be constructed from 38 unrelated families carrying the conserved haplotype or parts thereof. When these were arrayed based not on their descendance, but on their degree of haplotype sharing, it became apparent that a single segment flanked by the markers H4CA to H5CA was shared among all patients, independent of their geographic origin.

6.2.2. BAC CONTIG CONSTRUCTION

A BAC/PAC contig was constructed for the critical region between the markers H4CA and H5CA defined by haplotype analysis. Initially, BACs were identified for D8S88, D8S1811, D8S1724 and AFM289zb5 followed by screens for ESTs WI 8975 and StG9973. BAC ends were sequenced to generate new STSs which were used for further STS content mapping and in walking experiments to identify further BAC clones or PAC clones. A total of 36 BACs and 22 PACs were used to construct a contig, which was estimated to span 1.2 Mb based on the long range restriction map. A subset of 12 BACs and PACs was used to construct the contig spanning the NBS critical region. Two known genes, calbindin (CALB) and 2,4@dienoyl-CoA reductase (DECR) could be placed on this map.

6.2.3. TRANSCRIPT DETECTION

Transcripts were identified through 2 strategies: (1) All known transcripts and ESTs mapped with radiation hybrids by Schuler et al. (1996) to the interval D8S270–D8S271, or to the two immediately adjacent intervals, were mapped on the BAC/PAC contig. A total of 9 ESTs were mapped to specific genomic clones by PCR amplification. (2) Based on the genomic sequence obtained from low redundancy sequencing of the entire BAC/PAC contig, additional, previously unmapped ESTs were identified through repeated database searches. By these approaches, a total of 31 ESTs were identified, which were later consolidated into 21 cDNA contigs. Sequences were verified against the genomic sequence to identify exons and introns and were investigated for putative open reading frames and homology to other species.

6.2.4. MUTATION DETECTION

In order to search for mutations, mRNA was extracted from lymphoblastoid cell lines from 14 patients homozygous for the conserved haplotype, and one patient that was heterozygous and amplified overlapping cDNA fragments of 300 bp average size for all transcripts identified in the 1.2 Mb region. When genomic sequence information was available for a given transcript, exonic fragments were also amplified from genomic DNA from additional patients for whom lymphoblastoid cell lines were not available. All PCR-fragments were analyzed by SSCP and/or direct sequencing. A total of 8 genes were screened for variation. Polymorphisms in three cDNA contigs, BR1, BR4, BR23 and one known gene CALB were identified based on their presence in both patients and controls. These polymorphisms were used as markers to further refine the haplotyping.

In one cDNA contig, BR7, an aberrant banding pattern was identified by SSCP in a cDNA fragment amplified from all patients with the conserved haplotype but none of the controls. Sequencing of this product revealed a homozygous five bp deletion (FIGS. 1A and 1B) predicted to result in a frameshift and in premature termination 15 amino acids downstream. This mutation was present on all chromosomes bearing the conserved haplotype or parts thereof. It was not detected in any of 50 normal control individuals nor on any of 28 normal (untransmitted) chromosomes from NBS parents examined, further suggesting that this was a causative mutation for NBS.

6.2.5. IDENTIFICATION OF THE NBS GENE

After the initial identification of a common truncating mutation in BR7, the transcript was further extended in 5' direction and linked to the 2.6 kb BR1 cDNA contig, which contained a poly-A tail, defining the 3' end of the gene. The entire cDNA sequence (FIG. 2, SEQ ID NO:1) of 4386 bp contains an ORF of 2277 bp (access. no. AF0513334). The first ATG at position 26 of this sequence was assumed to be the translation initiation site. The encoded protein of 754 amino acids has a predicted molecular weight of 85 kD. We termed the gene NBS1 and its protein product, nibrin. The nucleotide sequence of a genomic contig of 66 kb containing the entire NBS1 gene was determined (access. no. AF049895). Comparison of the genomic sequence to that of the cDNA defined the exon-intron organization of the gene. A total of 16 exons were identified, which, together with introns spanned over 50 kb. Fluorescent in situ hybridization (FISH) using a directly labeled BAC clone containing the NBS1 gene as a probe localized the gene to 8q21.13-q21.3.

Figure 2:
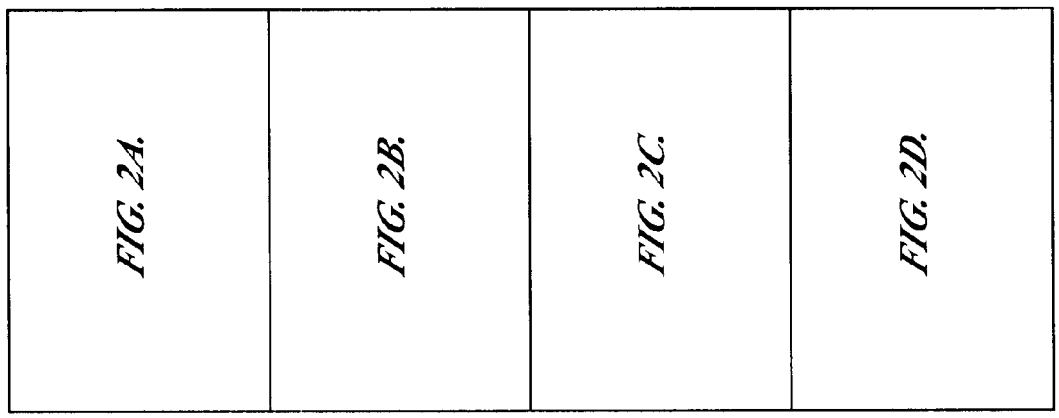
Figure 2B:
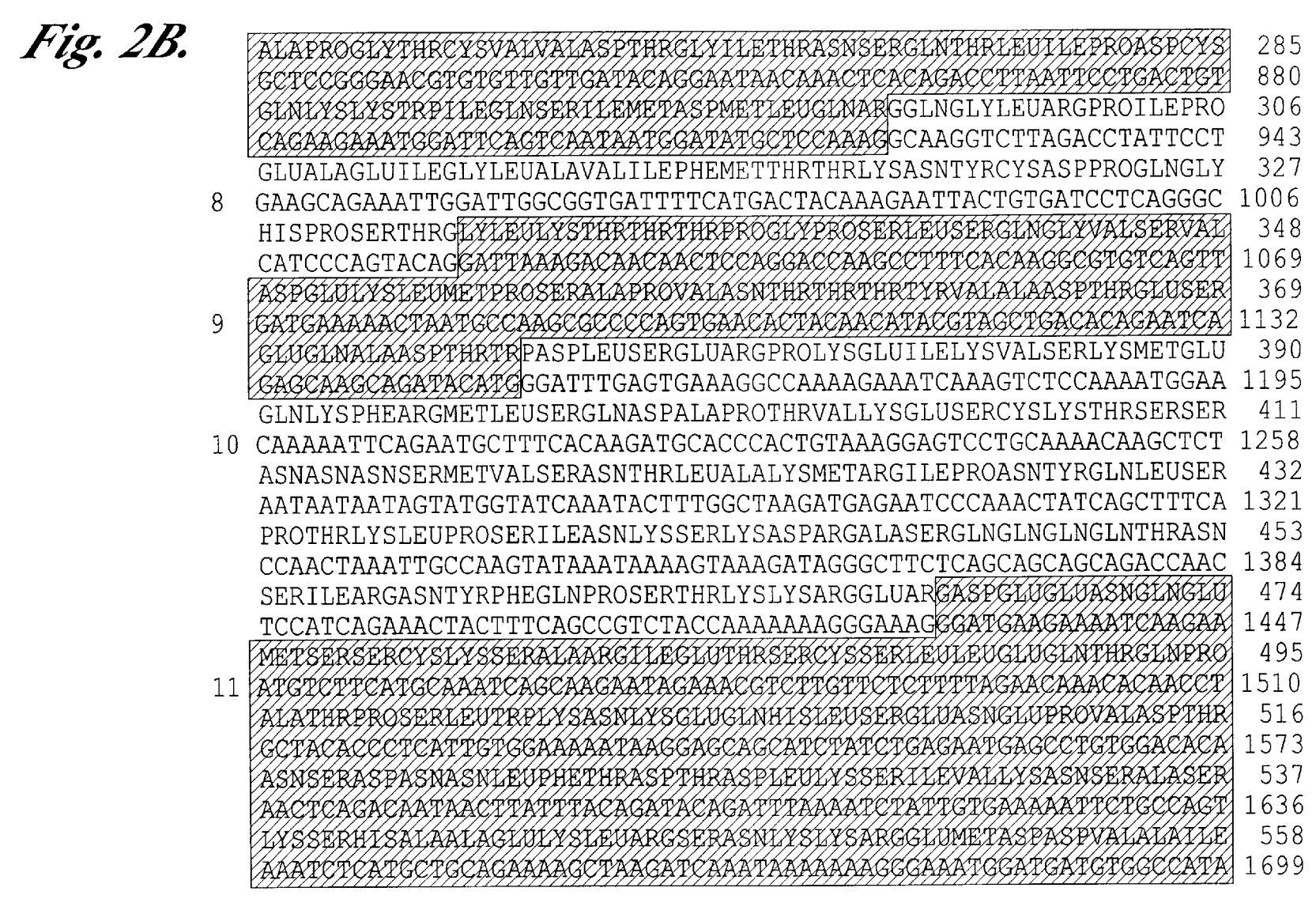

Northern blots containing mRNA from 16 different tissues were probed with a 576 bp fragment from the coding region of the NBS1 gene. Transcripts of 2.4 and 4.4 kb were observed in all tissues (FIG. 3). The presence of the smaller 2.4 kb transcript was unexpected. However, in the 3' untranslated region of the cDNA, two potential poly-adenylation signals were found at positions 2440 and 4386 (FIG. 2). Comparison of ESTs in the database containing the 3' end of the transcript confirmed that both poly-adenylation signals are used to generate the alternative transcripts. Densitometry and phosphorimaging of Northern blots were used to quantitate transcript levels for NBS1 relative to a GAPDH control. Three tissues, spleen, testis and ovary had approximately two-fold more transcripts than other tissues. The 4.4 kb transcript predominated in most tissues except testis where the 2.4 kb transcript was more common. No significant increase in transcript levels was observed in fibroblasts after irradiation with 5 Gy.

Sequence comparisons of nibrin with other protein sequences in the database failed to identify any global similarities. Comprehensive sequence comparisons revealed two domains in the aminoterminal region, a fork-head associated domain (FHA) (Hoftnann and Bucher, 1995, Trends Biochem. Sciences 20:347–349), residues 24–100, and a breast cancer carboxyterminal domain (BRCT) (Bork et al., 1997, FASEB, J. 11:68–76), residues 105–190. Both domains have been found separately in DNA damage-responsive cell-cycle check-point proteins, their adjacent localization in nibrin, though, is unique (FIGS. 4A–4C).

6.2.6. MUTATION SCREENING

All NBS chromosomes with the conserved Slavic marker haplotype were found to bear the 657del5 mutation, indicating a founder effect for this mutation. For subsequent mutation analysis a set of intronic primers flanking each of the 16 exons was designed from the genomic sequence obtained through sequencing of the BAC contig. These primers were used to screen the additional 5 patients who had at least one chromosome that did not carry the 657del5 mutation or the conserved haplotype. Mutations were identified in all of these patients, most being small insertions or deletions (Table 1). All mutations were predicted to cause premature truncation downstream of the FHA and BRCT domains.

Thus far, all NBS patients from families with genetic linkage to 8q21 have mutations in the NBS1 gene. This includes 46 patients homozygous for the common 657del5 mutation including the first patient described, 2 patients heterozygous for 657del5 and a second mutation, and 3 patients homozygous each for unique NBS mutations (Table 1). Several polymorphisms (Table 1) were identified, including one non-conservative amino acid substitution at position 185 (glutamine for glutamic acid). Control probands of German origin who were homozygous for each of these alleles were identified.

The present invention is not to be limited in scope by the exemplified embodiments or deposited organisms which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

TABLE 1

NBS gene mutations and polymorphisms

| Name | Nucleotide change | Exon | Consequence | Origin |
|---|---|---|---|---|
| 657del5 | 657–661delACAAA | 6 | frameshift | Slavic |
| 698del4 | 698–701delAACA | 6 | frameshift | English |
| 835del4 | 835–838delCAGA | 7 | frameshift | Italian |
| 842insT | 842–843insT | 7 | frameshift | Mexican |
| 1142delC | 1142delC | 10 | frameshift | Canadian |
| 976C > T | C > T at 976 | 8 | Q326X | Dutch |
| 681delT |  | 6 | frameshift | Russian |
| 900del25 |  | 8 | frameshift | African |

TABLE 1-continued

NBS gene mutations and polymorphisms
Polymorphisms

| 553G/C | G > C at 553 | 5 | Glu > Gln at 185 |
|---|---|---|---|
| 1197T/C | T > C at 1197 | 10 | — |
| 2016A/G | A > G at 2016 | 13 | — |
| 102G/A |  |  |  |
| 1VS5 + 9T/C |  |  |  |
| 1VS5 + 51delT |  |  |  |
| 1VS9 + 18C/T |  |  |  |
| 1VS12 − 7A/G |  |  |  |

What is claimed is:

1. An isolated polynucleotide, comprising a nucleotide sequence that encodes a polypeptide comprising the amino acid sequence as shown in SEQ ID NO:2.

2. The polynucleotide of claim 1 in which the nucleotide sequence is shown in SEQ ID NO:1.

3. An isolated polynucleotide, comprising a nucleotide sequence of at least 12 nucleotides that hybridizes under stringent conditions to a second polynucleotide having a nucleotide sequence as shown in SEQ ID NO:1 or to the complementary sequence of the second polynucleotide.

4. The polynucleotide of claim 3 which encodes a nibrin.

5. The isolated polynucleotide of claim 3 which is cDNA.

6. A recombinant vector containing the polynucleotide of claim 1.

7. A recombinant expression vector containing the polynucleotide of claim 1 in which the nucleotide sequence is operatively associated with a regulatory nucleotide sequence that controls expression of the polynucleotide in a host cell.

8. A genetically-engineered host cell containing the expression vector of claim 7, or progeny thereof.

9. The genetically-engineered host cell of claim 8 which is a prokaryote.

10. The genetically-engineered host cell of claim 8 which is an eukaryote.

* * * * *

SEQUENCE LISTING

<160> NUMBER OF SEQ ID NOS: 64

<210> SEQ ID NO 1
<211> LENGTH: 4386
<212> TYPE: DNA
<213> ORGANISM: Homo sapien
<220> FEATURE:
<221> NAME/KEY: CDS
<222> LOCATION: (26)...(2287)

<400> SEQUENCE: 1

```
gcccccagccc tgaggagccg gaccg atg tgg aaa ctg ctg ccc gcc gcg ggc     52
                             Met Trp Lys Leu Leu Pro Ala Ala Gly
                               1               5 ccg gca gga gga gaa cca tac aga ctt ttg act ggc gtt gag tac gtt    100
Pro Ala Gly Gly Glu Pro Tyr Arg Leu Leu Thr Gly Val Glu Tyr Val
 10                  15                  20                  25 gtt gga agg aaa aac tgt gcc att ctg att gaa aat gat cag tcg atc    148
Val Gly Arg Lys Asn Cys Ala Ile Leu Ile Glu Asn Asp Gln Ser Ile
                 30                  35                  40 agc cga aat cat gct gtg tta act gct aac ttt tct gta acc aac ctg    196
Ser Arg Asn His Ala Val Leu Thr Ala Asn Phe Ser Val Thr Asn Leu
             45                  50                  55 agt caa aca gat gaa atc cct gta ttg aca tta aaa gat aat tct aag    244
Ser Gln Thr Asp Glu Ile Pro Val Leu Thr Leu Lys Asp Asn Ser Lys
         60                  65                  70 tat ggt acc ttt gtt aat gag gaa aaa atg cag aat ggc ttt tcc cga    292
Tyr Gly Thr Phe Val Asn Glu Glu Lys Met Gln Asn Gly Phe Ser Arg
     75                  80                  85 act ttg aag tcg ggg gat ggt att act ttt gga gtg ttt gga agt aaa    340
Thr Leu Lys Ser Gly Asp Gly Ile Thr Phe Gly Val Phe Gly Ser Lys
 90                  95                 100                 105 ttc aga ata gag tat gag cct ttg gtt gca tgc tct tct tgt tta gat    388
Phe Arg Ile Glu Tyr Glu Pro Leu Val Ala Cys Ser Ser Cys Leu Asp
                110                 115                 120 gtc tct ggg aaa act gct tta aat caa gct ata ttg caa ctt gga gga    436
Val Ser Gly Lys Thr Ala Leu Asn Gln Ala Ile Leu Gln Leu Gly Gly
            125                 130                 135 ttt act gta aac aat tgg aca gaa gaa tgc act cac ctt gtc atg gta    484
```

```
Phe Thr Val Asn Asn Trp Thr Glu Glu Cys Thr His Leu Val Met Val
        140                 145                 150 tca gtg aaa gtt acc att aaa aca ata tgt gca ctc att tgt gga cgt        532
Ser Val Lys Val Thr Ile Lys Thr Ile Cys Ala Leu Ile Cys Gly Arg
        155                 160                 165 cca att gta aag cca gaa tat ttt act gaa ttc ctg aaa gca gtt gag        580
Pro Ile Val Lys Pro Glu Tyr Phe Thr Glu Phe Leu Lys Ala Val Glu
170                 175                 180                 185 tcc aag aag cag cct cca caa att gaa agt ttt tac cca cct ctt gat        628
Ser Lys Lys Gln Pro Pro Gln Ile Glu Ser Phe Tyr Pro Pro Leu Asp
                190                 195                 200 gaa cca tct att gga agt aaa aat gtt gat ctg tca gga cgg cag gaa        676
Glu Pro Ser Ile Gly Ser Lys Asn Val Asp Leu Ser Gly Arg Gln Glu
            205                 210                 215 aga aaa caa atc ttc aaa ggg aaa aca ttt ata ttt ttg aat gcc aaa        724
Arg Lys Gln Ile Phe Lys Gly Lys Thr Phe Ile Phe Leu Asn Ala Lys
        220                 225                 230 cag cat aag aaa ttg agt tcc gca gtt gtc ttt gga ggt ggg gaa gct        772
Gln His Lys Lys Leu Ser Ser Ala Val Val Phe Gly Gly Gly Glu Ala
    235                 240                 245 agg ttg ata aca gaa gag aat gaa gaa gaa cat aat ttc ttt ttg gct        820
Arg Leu Ile Thr Glu Glu Asn Glu Glu Glu His Asn Phe Phe Leu Ala
250                 255                 260                 265 ccg gga acg tgt gtt gtt gat aca gga ata aca aac tca cag acc tta        868
Pro Gly Thr Cys Val Val Asp Thr Gly Ile Thr Asn Ser Gln Thr Leu
                270                 275                 280 att cct gac tgt cag aag aaa tgg att cag tca ata atg gat atg ctc        916
Ile Pro Asp Cys Gln Lys Lys Trp Ile Gln Ser Ile Met Asp Met Leu
            285                 290                 295 caa agg caa ggt ctt aga cct att cct gaa gca gaa att gga ttg gcg        964
Gln Arg Gln Gly Leu Arg Pro Ile Pro Glu Ala Glu Ile Gly Leu Ala
        300                 305                 310 gtg att ttc atg act aca aag aat tac tgt gat cct cag ggc cat ccc       1012
Val Ile Phe Met Thr Thr Lys Asn Tyr Cys Asp Pro Gln Gly His Pro
    315                 320                 325 agt aca gga tta aag aca aca act cca gga cca agc ctt tca caa ggc       1060
Ser Thr Gly Leu Lys Thr Thr Thr Pro Gly Pro Ser Leu Ser Gln Gly
330                 335                 340                 345 gtg tca gtt gat gaa aaa cta atg cca agc gcc cca gtg aac act aca       1108
Val Ser Val Asp Glu Lys Leu Met Pro Ser Ala Pro Val Asn Thr Thr
                350                 355                 360 aca tac gta gct gac aca gaa tca gag caa gca gat aca tgg gat ttg       1156
Thr Tyr Val Ala Asp Thr Glu Ser Glu Gln Ala Asp Thr Trp Asp Leu
            365                 370                 375 agt gaa agg cca aaa gaa atc aaa gtc tcc aaa atg gaa caa aaa ttc       1204
Ser Glu Arg Pro Lys Glu Ile Lys Val Ser Lys Met Glu Gln Lys Phe
        380                 385                 390 aga atg ctt tca caa gat gca ccc act gta aag gag tcc tgc aaa aca       1252
Arg Met Leu Ser Gln Asp Ala Pro Thr Val Lys Glu Ser Cys Lys Thr
    395                 400                 405 agc tct aat aat aat agt atg gta tca aat act ttg gct aag atg aga       1300
Ser Ser Asn Asn Asn Ser Met Val Ser Asn Thr Leu Ala Lys Met Arg
410                 415                 420                 425 atc cca aac tat cag ctt tca cca act aaa ttg cca agt ata aat aaa       1348
Ile Pro Asn Tyr Gln Leu Ser Pro Thr Lys Leu Pro Ser Ile Asn Lys
                430                 435                 440 agt aaa gat agg gct tct cag cag cag cag acc aac tcc atc aga aac       1396
Ser Lys Asp Arg Ala Ser Gln Gln Gln Gln Thr Asn Ser Ile Arg Asn
            445                 450                 455
```

```
tac ttt cag ccg tct acc aaa aaa agg gaa agg gat gaa gaa aat caa      1444
Tyr Phe Gln Pro Ser Thr Lys Lys Arg Glu Arg Asp Glu Glu Asn Gln
            460                 465                 470 gaa atg tct tca tgc aaa tca gca aga ata gaa acg tct tgt tct ctt      1492
Glu Met Ser Ser Cys Lys Ser Ala Arg Ile Glu Thr Ser Cys Ser Leu
    475                 480                 485 tta gaa caa aca caa cct gct aca ccc tca ttg tgg aaa aat aag gag      1540
Leu Glu Gln Thr Gln Pro Ala Thr Pro Ser Leu Trp Lys Asn Lys Glu
490                 495                 500                 505 cag cat cta tct gag aat gag cct gtg gac aca aac tca gac aat aac      1588
Gln His Leu Ser Glu Asn Glu Pro Val Asp Thr Asn Ser Asp Asn Asn
                510                 515                 520 tta ttt aca gat aca gat tta aaa tct att gtg aaa aat tct gcc agt      1636
Leu Phe Thr Asp Thr Asp Leu Lys Ser Ile Val Lys Asn Ser Ala Ser
                    525                 530                 535 aaa tct cat gct gca gaa aag cta aga tca aat aaa aaa agg gaa atg      1684
Lys Ser His Ala Ala Glu Lys Leu Arg Ser Asn Lys Lys Arg Glu Met
            540                 545                 550 gat gat gtg gcc ata gaa gat gaa gta ttg gaa cag tta ttc aag gac      1732
Asp Asp Val Ala Ile Glu Asp Glu Val Leu Glu Gln Leu Phe Lys Asp
    555                 560                 565 aca aaa cca gag tta gaa att gat gtg aaa gtt caa aaa cag gag gaa      1780
Thr Lys Pro Glu Leu Glu Ile Asp Val Lys Val Gln Lys Gln Glu Glu
570                 575                 580                 585 gat gtc aat gtt aga aaa agg cca agg atg gat ata gaa aca aat gac      1828
Asp Val Asn Val Arg Lys Arg Pro Arg Met Asp Ile Glu Thr Asn Asp
                590                 595                 600 act ttc agt gat gaa gca gta cca gaa agt agc aaa ata tct caa gaa      1876
Thr Phe Ser Asp Glu Ala Val Pro Glu Ser Ser Lys Ile Ser Gln Glu
                    605                 610                 615 aat gaa att ggg aag aaa cgt gaa ctc aag gaa gac tca cta tgg tca      1924
Asn Glu Ile Gly Lys Lys Arg Glu Leu Lys Glu Asp Ser Leu Trp Ser
            620                 625                 630 gct aaa gaa ata tct aac aat gac aaa ctt cag gat gat agt gag atg      1972
Ala Lys Glu Ile Ser Asn Asn Asp Lys Leu Gln Asp Asp Ser Glu Met
    635                 640                 645 ctt cca aaa aag ctg tta ttg act gaa ttt aga tca ctg gtg att aaa      2020
Leu Pro Lys Lys Leu Leu Leu Thr Glu Phe Arg Ser Leu Val Ile Lys
650                 655                 660                 665 aac tct act tcc aga aat cca tct ggc ata aat gat gat tat ggt caa      2068
Asn Ser Thr Ser Arg Asn Pro Ser Gly Ile Asn Asp Asp Tyr Gly Gln
                670                 675                 680 cta aaa aat ttc aag aaa ttc aaa aag gtc aca tat cct gga gca gga      2116
Leu Lys Asn Phe Lys Lys Phe Lys Lys Val Thr Tyr Pro Gly Ala Gly
                    685                 690                 695 aaa ctt cca cac atc att gga gga tca gat cta ata gct cat cat gct      2164
Lys Leu Pro His Ile Ile Gly Gly Ser Asp Leu Ile Ala His His Ala
            700                 705                 710 cga aag aat aca gaa cta gaa gag tgg cta agg cag gaa atg gag gta      2212
Arg Lys Asn Thr Glu Leu Glu Glu Trp Leu Arg Gln Glu Met Glu Val
    715                 720                 725 caa aat caa cat gca aaa gaa gag tct ctt gct gat gat ctt ttt aga      2260
Gln Asn Gln His Ala Lys Glu Glu Ser Leu Ala Asp Asp Leu Phe Arg
730                 735                 740                 745 tac aat cct tat tta aaa agg aga aga taactgagga ttttaaaaag            2307
Tyr Asn Pro Tyr Leu Lys Arg Arg Arg
                750 aagccatgga aaaacttcct agtaagcatc tacttcaggc aacaaggtt atatgaatat     2367 atagtgtata gaagcgattt aagttacaat gttttatggc ctaaatttat taaatbaaat   2427
```

-continued

```
gcacaaaact ttgattcttt tgtatgtaac aattgtttgt tctgttttca ggctttgtca    2487
ttgcatcttt ttttcatttt taaatgtgtt ttgtttatta aatagttaat atagtcacag    2547
ttcaaaattc taaatgtacg taaggtaaag actaaagtca cccttccacc attgtcctag    2607
ctacttggtt cccctcagaa aaaaattcat gatactcatt tcttatgaat ctttccaggg    2667 attttttgagt cctattcaaa ttcctatttt taaataattt cctacacaaa tgatagcata   2727
acatatgcag tgttctacac cttgcttttt tacttagtag attaaaaatt ataggaatat    2787
caatataatg tttttaatat ttttctttt ccattatgct gtagtcttac ctaaactctg    2847
gtgatccaaa caaatggct tcagtggtgc agatgtcacc tacatgttat tctagtacta    2907
gaaactgaag accatgtgga gacttcatca aacatgggtt tagttttcac cagaatggaa    2967
agacctgtac cccttttttgg tggtcttact gagctgggtg ggtgtctgtt ttgagcttat   3027
ttagagtcct agttttccta cttataaagt agaaatggtg agattgtttt cttttttctac   3087 cttaaaggga gatggtaaga aacaatgaat gtctttttc aaactttatt gacaagtgat    3147
tttcaagtct gtgttcaaaa atatattcat gtacctgtga tccagcaaga agggagttcc   3207
agtcaagagt cactacaact gattagttgt ttagagaatg agaaatggaa cagtgaggaa    3267
tggaggccat atttccatga cttcccttgt aaacagaagc aacagaaggg acaagaggct   3327
ggcctctaca tcactctcac cttccaaatc ttgtggaagt gcatctactt gccagaacca   3387
aattaactta cttccaagtt ctggctgctt gcaggtggaa ctccagctgc aagggagtta   3447
gggaaatgaa ggtctttttt taaaagcttc tcagccttcc tagggaacag aaattgggtg   3507
agccaatctg caatttctac tacaggcatt gagaccagtt agattattga aatattatag   3567
agagttatga acacttaaat tatgatagtg gtatgacatt ggatagaaca tgggatactt   3627
tagaagtaga attgacaggg catattagtt gatgaaatgg agtcatttga gtctcttaat   3687
agccatgtat cataattacc aagtgaagct ggtggaacat atggtctcca ttttacagtt   3747
aaggaatata atggacagat taatattgtt ctctgtcatg cccacaatcc ctttctaagg   3807
aagactgccc tactatagca gttttttatat ttgtcaatt atgaatataa tgaatgagag   3867
ttctggtacc tcctgtcttt acaaatattg gtgttgtcag tattttttcct ttttaaccat   3927 tccaatcggt gtgtagtgat gtttcattt ggttttaatt tgtatatccc tgatagctat    3987
aattgggtca tagaaattct ttatacattc tagatgcaag tctcttgtcg gatatatgta    4047
ttgagatatt acacctagtc tgtggcttga ctgttttctt tatgtctttt gatgaataga    4107
agttttaaat tttgacaagg tcaaatttat tttttttcttt tgtttgatat tttttctctc   4167
caatttaacc ccaagatttc agatattctg ctctattata taaactttat atttttatat   4227
ttgtgatcta ccttgaattg atatgtatgt tgtgaattat ggatcagggt tctttttttc    4287
ccccatacaa gtaccagtc attgtaacac tgtttattga aagaattatc ctttcctcat    4347
taaattacct tgccaattag taaaaaatca attaaccat                           4386
```

<210> SEQ ID NO 2
<211> LENGTH: 754
<212> TYPE: PRT
<213> ORGANISM: Homo sapien

<400> SEQUENCE: 2

Met Trp Lys Leu Leu Pro Ala Ala Gly Pro Ala Gly Gly Glu Pro Tyr
 1               5                  10                  15

Arg Leu Leu Thr Gly Val Glu Tyr Val Val Gly Arg Lys Asn Cys Ala

-continued

```
                20                  25                  30
Ile Leu Ile Glu Asn Asp Gln Ser Ile Ser Arg Asn His Ala Val Leu
             35                  40                  45
Thr Ala Asn Phe Ser Val Thr Asn Leu Ser Gln Thr Asp Glu Ile Pro
         50                  55                  60
Val Leu Thr Leu Lys Asp Asn Ser Lys Tyr Gly Thr Phe Val Asn Glu
 65                  70                  75                  80
Glu Lys Met Gln Asn Gly Phe Ser Arg Thr Leu Lys Ser Gly Asp Gly
                 85                  90                  95
Ile Thr Phe Gly Val Phe Gly Ser Lys Phe Arg Ile Glu Tyr Glu Pro
                100                 105                 110
Leu Val Ala Cys Ser Ser Cys Leu Asp Val Ser Gly Lys Thr Ala Leu
                115                 120                 125
Asn Gln Ala Ile Leu Gln Leu Gly Gly Phe Thr Val Asn Asn Trp Thr
            130                 135                 140
Glu Glu Cys Thr His Leu Val Met Val Ser Val Lys Val Thr Ile Lys
145                 150                 155                 160
Thr Ile Cys Ala Leu Ile Cys Gly Arg Pro Ile Val Lys Pro Glu Tyr
                165                 170                 175
Phe Thr Glu Phe Leu Lys Ala Val Glu Ser Lys Lys Gln Pro Pro Gln
            180                 185                 190
Ile Glu Ser Phe Tyr Pro Pro Leu Asp Glu Pro Ser Ile Gly Ser Lys
            195                 200                 205
Asn Val Asp Leu Ser Gly Arg Gln Glu Arg Lys Gln Ile Phe Lys Gly
        210                 215                 220
Lys Thr Phe Ile Phe Leu Asn Ala Lys Gln His Lys Lys Leu Ser Ser
225                 230                 235                 240
Ala Val Val Phe Gly Gly Gly Glu Ala Arg Leu Ile Thr Glu Glu Asn
                245                 250                 255
Glu Glu Glu His Asn Phe Phe Leu Ala Pro Gly Thr Cys Val Val Asp
            260                 265                 270
Thr Gly Ile Thr Asn Ser Gln Thr Leu Ile Pro Asp Cys Gln Lys Lys
            275                 280                 285
Trp Ile Gln Ser Ile Met Asp Met Leu Gln Arg Gln Gly Leu Arg Pro
        290                 295                 300
Ile Pro Glu Ala Glu Ile Gly Leu Ala Val Ile Phe Met Thr Thr Lys
305                 310                 315                 320
Asn Tyr Cys Asp Pro Gln Gly His Pro Ser Thr Gly Leu Lys Thr Thr
                325                 330                 335
Thr Pro Gly Pro Ser Leu Ser Gln Gly Val Ser Val Asp Glu Lys Leu
            340                 345                 350
Met Pro Ser Ala Pro Val Asn Thr Thr Tyr Val Ala Asp Thr Glu
            355                 360                 365
Ser Glu Gln Ala Asp Thr Trp Asp Leu Ser Glu Arg Pro Lys Glu Ile
        370                 375                 380
Lys Val Ser Lys Met Glu Gln Lys Phe Arg Met Leu Ser Gln Asp Ala
385                 390                 395                 400
Pro Thr Val Lys Glu Ser Cys Lys Thr Ser Ser Asn Asn Ser Met
                405                 410                 415
Val Ser Asn Thr Leu Ala Lys Met Arg Ile Pro Asn Tyr Gln Leu Ser
            420                 425                 430
Pro Thr Lys Leu Pro Ser Ile Asn Lys Ser Lys Asp Arg Ala Ser Gln
        435                 440                 445
```

-continued

```
Gln Gln Gln Thr Asn Ser Ile Arg Asn Tyr Phe Gln Pro Ser Thr Lys
    450                 455                 460
Lys Arg Glu Arg Asp Glu Asn Gln Glu Met Ser Ser Cys Lys Ser
465                 470                 475                 480
Ala Arg Ile Glu Thr Ser Cys Ser Leu Leu Glu Gln Thr Gln Pro Ala
            485                 490                 495
Thr Pro Ser Leu Trp Lys Asn Lys Glu Gln His Leu Ser Glu Asn Glu
                500                 505                 510
Pro Val Asp Thr Asn Ser Asp Asn Asn Leu Phe Thr Asp Thr Asp Leu
            515                 520                 525
Lys Ser Ile Val Lys Asn Ser Ala Ser Lys Ser His Ala Ala Glu Lys
530                 535                 540
Leu Arg Ser Asn Lys Lys Arg Glu Met Asp Asp Val Ala Ile Glu Asp
545                 550                 555                 560
Glu Val Leu Glu Gln Leu Phe Lys Asp Thr Lys Pro Glu Leu Glu Ile
                565                 570                 575
Asp Val Lys Val Gln Lys Gln Glu Glu Asp Val Asn Val Arg Lys Arg
            580                 585                 590
Pro Arg Met Asp Ile Glu Thr Asn Asp Thr Phe Ser Asp Glu Ala Val
        595                 600                 605
Pro Glu Ser Ser Lys Ile Ser Gln Glu Asn Glu Ile Gly Lys Lys Arg
610                 615                 620
Glu Leu Lys Glu Asp Ser Leu Trp Ser Ala Lys Glu Ile Ser Asn Asn
625                 630                 635                 640
Asp Lys Leu Gln Asp Asp Ser Glu Met Leu Pro Lys Lys Leu Leu Leu
                645                 650                 655
Thr Glu Phe Arg Ser Leu Val Ile Lys Asn Ser Thr Ser Arg Asn Pro
            660                 665                 670
Ser Gly Ile Asn Asp Asp Tyr Gly Gln Leu Lys Asn Phe Lys Lys Phe
        675                 680                 685
Lys Lys Val Thr Tyr Pro Gly Ala Gly Lys Leu Pro His Ile Ile Gly
690                 695                 700
Gly Ser Asp Leu Ile Ala His His Ala Arg Lys Asn Thr Glu Leu Glu
705                 710                 715                 720
Glu Trp Leu Arg Gln Glu Met Glu Val Gln Asn Gln His Ala Lys Glu
                725                 730                 735
Glu Ser Leu Ala Asp Asp Leu Phe Arg Tyr Asn Pro Tyr Leu Lys Arg
            740                 745                 750
Arg Arg

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tcatccaagg cagcctgcgt                                              20

<210> SEQ ID NO 4
<211> LENGTH: 20
<212> TYPE: DNA
<213> ORGANISM: Artificial Sequence
<220> FEATURE:
<223> OTHER INFORMATION: Primer
```

<400> SEQUENCE: 4
tgccatacag cgtactcgcc					20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ctttgatagc cttcagtgag					20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctctctctca catacaaacc					20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cagtaattgt tgtctgccgt					20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aggatttggc tgaaacaaag					20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gcttaatgat gaggaactga					20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cctaaatggt atacaaaggg					20

<210> SEQ ID NO 11

```
<211> LENGTH: 20
<212> TYPE: DNA
<213> ORGANISM: Artificial Sequence
<220> FEATURE:
<223> OTHER INFORMATION: Primer

<400> SEQUENCE: 11
ttatggatgt aaacagcctc                                               20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
taccgaacta taacacagca                                               20

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
cagatagtca ctccgtttac aa                                            22

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
atgaataggc cagttatcac ag                                            22

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tcaagaagta gcaccaagtc                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aattgcttga acccagaagg                                               20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
```

```
gaggttgctt tatcttgaca                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ccctagcaag tatatagata                                              20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cttagcatgg tatagtctaa                                              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ctcaagagac aacctgataa                                              20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
tgctttcttg ggatggtaaa                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gcagaagcat acttaatcag                                              20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
atggttactt agctgtgttc                                              20

<210> SEQ ID NO 24
<211> LENGTH: 20
<212> TYPE: DNA
```

```
<213> ORGANISM: Artificial Sequence
<220> FEATURE:
<223> OTHER INFORMATION: Primer

<400> SEQUENCE: 24
taatggatgc tcatactgtc                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
atgcctggtc atacataaca                                              20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
aattgatgag atgacagtcc                                              20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
agattcccaa atgacaagtg                                              20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
agttcatatc cttcctagag                                              20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
aacatctttg gcacttatgc                                              20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
agaagaattt gcttgaaggc                                              20
```

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ctattggttg tctttgagtg                                          20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
atttcacaca attcgggaac                                          20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tcattcccat cctatttgcc                                          20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
tggaagggtg actttagtct                                          20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
aggtaaagac taaagtcacc                                          20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
tgtttgatga agtctccaca                                          20

<210> SEQ ID NO 37
<211> LENGTH: 20
<212> TYPE: DNA
<213> ORGANISM: Artificial Sequence
<220> FEATURE:

```
<223> OTHER INFORMATION: Primer

<400> SEQUENCE: 37
agtactagaa actgaagacc                                                    20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
atttggaagg tgagagtgat                                                    20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gtaaacagaa gcaacagaag                                                    20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
ggcaaggtaa tttaatgagg                                                    20

<210> SEQ ID NO 41
<211> LENGTH: 64
<212> TYPE: PRT
<213> ORGANISM: Homo sapien

<400> SEQUENCE: 41

Tyr Val Val Gly Arg Lys Asn Cys Ala Ile Leu Ile Glu Asn Asp Gln
 1               5                  10                  15

Ser Ile Ser Arg Asn His Ala Val Leu Thr Ala Asn Val Leu Thr Leu
            20                  25                  30

Lys Asp Asn Ser Lys Tyr Gly Thr Phe Val Asn Glu Glu Lys Met Gln
        35                  40                  45

Asn Gly Phe Ser Arg Thr Leu Lys Ser Gly Asp Gly Ile Thr Phe Gly
    50                  55                  60

<210> SEQ ID NO 42
<211> LENGTH: 63
<212> TYPE: PRT
<213> ORGANISM: Homo sapien

<400> SEQUENCE: 42

Cys Leu Phe Gly Arg Gly Ile Glu Cys Asp Ile Arg Ile Gln Leu Pro
 1               5                  10                  15

Val Val Ser Lys Gln His Cys Lys Ile Glu Ile His Glu Ala Ile Leu
            20                  25                  30

His Asn Phe Ser Ser Thr Asn Pro Thr Gln Val Asn Gly Ser Val Ile
        35                  40                  45
```

```
Asp Glu Pro Val Arg Leu Lys His Gly Asp Val Ile Thr Ile Ile
    50                  55                  60
```

<210> SEQ ID NO 43
<211> LENGTH: 63
<212> TYPE: PRT
<213> ORGANISM: Saccharomyces cerevisiae

<400> SEQUENCE: 43

```
Thr Thr Ile Gly Arg Ser Arg Ser Cys Asp Val Ile Leu Ser Glu Pro
 1               5                  10                  15

Asp Ile Ser Thr Phe His Ala Glu Phe His Leu Leu Leu Ile Asn Val
            20                  25                  30

Ile Asp Lys Ser Arg Asn Gly Thr Phe Ile Asn Gly Asn Arg Leu Val
        35                  40                  45

Lys Lys Asp Tyr Ile Leu Lys Asn Gly Asp Arg Ile Val Phe Gly
    50                  55                  60
```

<210> SEQ ID NO 44
<211> LENGTH: 64
<212> TYPE: PRT
<213> ORGANISM: Schizosaccharomyces pombe

<400> SEQUENCE: 44

```
Trp Gly Phe Gly Arg His Lys Ser Cys Glu Val Val Leu Asn Gly Pro
 1               5                  10                  15

Arg Val Ser Asn Phe His Phe Glu Ile Tyr Gln Gly Val Val Phe Leu
            20                  25                  30

His Asp His Ser Ser Asn Gly Thr Phe Leu Asn Phe Glu Arg Leu Ala
        35                  40                  45

Lys Asn Ser Arg Thr Ile Leu Ser Asn Gly Asp Glu Ile Arg Ile Gly
    50                  55                  60
```

<210> SEQ ID NO 45
<211> LENGTH: 64
<212> TYPE: PRT
<213> ORGANISM: Saccharomyces cerevisiae

<400> SEQUENCE: 45

```
Val Lys Val Gly Arg Asn Asp Lys Cys Gln Leu Val Leu Thr Asn Pro
 1               5                  10                  15

Ser Ile Ser Ser Val His Cys Val Phe Trp Cys Val Met Phe Tyr Val
            20                  25                  30

Lys Asp Cys Ser Leu Asn Gly Thr Tyr Leu Asn Gly Leu Leu Leu Lys
        35                  40                  45

Arg Asp Lys Thr Tyr Leu Leu Lys His Cys Asp Val Ile Glu Leu Ser
    50                  55                  60
```

<210> SEQ ID NO 46
<211> LENGTH: 65
<212> TYPE: PRT
<213> ORGANISM: Saccharomyces cerevisiae

<400> SEQUENCE: 46

```
Trp Thr Phe Gly Arg Asn Pro Ala Cys Asp Tyr His Leu Gly Asn Ile
 1               5                  10                  15

Ser Arg Leu Ser Asn Lys His Phe Gln Ile Leu Leu Gly Asn Leu Leu
            20                  25                  30

Leu Asn Asp Ile Ser Thr Asn Gly Thr Trp Leu Asn Gly Gln Lys Val
        35                  40                  45
```

```
Glu Lys Asn Ser Asn Gln Leu Leu Ser Gln Gly Asp Glu Ile Thr Val
        50                  55                  60
Gly
65

<210> SEQ ID NO 47
<211> LENGTH: 68
<212> TYPE: PRT
<213> ORGANISM: Saccharomyces cerevisiae

<400> SEQUENCE: 47

Val Thr Ile Gly Arg Asn Thr Asp Ile Asp Ile Asp Leu Gly Pro Ala
 1               5                  10                  15

Lys Ile Val Ser Arg Lys His Ala Ala Ile Arg Phe Asn Ser Trp Glu
            20                  25                  30

Leu Gln Ile Phe Gly Arg Asn Gly Ala Lys Val Asn Phe Arg Arg Ile
        35                  40                  45

Pro Thr Gly Pro Asp Ser Pro Pro Thr Val Leu Gln Ser Gly Cys Ile
    50                  55                  60

Ile Asp Ile Gly
65

<210> SEQ ID NO 48
<211> LENGTH: 65
<212> TYPE: PRT
<213> ORGANISM: Saccharomyces cerevisiae

<400> SEQUENCE: 48

Ala Ile Ile Gly Arg Arg Ser Glu Val Asp Val Asn Leu Gly Pro Ser
 1               5                  10                  15

Lys Ser Ile Ser Arg Arg His Ala Gln Ile Phe Tyr Asn Arg Phe Glu
            20                  25                  30

Leu Ser Ile Ile Gly Lys Asn Gly Ala Phe Val Asp Asp Ile Phe Val
        35                  40                  45

Glu Lys Gly Asn Thr Val Pro Leu Arg Asn Lys Thr Lys Ile Gln Ile
    50                  55                  60

Gly
65

<210> SEQ ID NO 49
<211> LENGTH: 65
<212> TYPE: PRT
<213> ORGANISM: A. thaliana

<400> SEQUENCE: 49

Val Lys Leu Gly Arg Val Ser Pro Ser Asp Leu Ala Leu Lys Asp Ser
 1               5                  10                  15

Glu Val Ser Gly Lys His Ala Gln Ile Thr Trp Asn Lys Trp Glu Leu
            20                  25                  30

Val Asp Met Gly Ser Leu Asn Gly Thr Leu Val Asn Ser His Ser Ile
        35                  40                  45

Ser His Pro Asp Leu Val Glu Leu Ala Ser Asp Ile Ile Thr Leu
    50                  55                  60

Gly
65

<210> SEQ ID NO 50
<211> LENGTH: 69
```

```
<212> TYPE: PRT
<213> ORGANISM: Anabaena Sp.

<400> SEQUENCE: 50

Val His Ile Gly Lys Pro Asn Asp Ile Asp Val Asp Val Ser Gly Phe
1               5                   10                  15

Ala Asn Ser Glu Ile Val Ser Arg Val His Ala Asp Ile Arg Leu Glu
            20                  25                  30

Ala His Tyr Ile Glu Asp Val Gly Ser Ser Asn Gly Thr Tyr Ile Asn
        35                  40                  45

Asn Leu Pro Leu Leu Pro Gly Asn Arg His Arg Leu Arg Pro Gly Asp
    50                  55                  60

Arg Ile Ser Leu Gly
65

<210> SEQ ID NO 51
<211> LENGTH: 87
<212> TYPE: PRT
<213> ORGANISM: Homo sapien

<400> SEQUENCE: 51

Glu Tyr Glu Pro Leu Val Ala Cys Ser Ser Cys Leu Asp Val Ser Gly
1               5                   10                  15

Lys Thr Ala Leu Asn Gln Ala Ile Leu Gln Leu Gly Gly Phe Thr Val
            20                  25                  30

Asn Asn Trp Thr Glu Glu Cys Thr His Leu Val Met Val Ser Val Lys
        35                  40                  45

Val Thr Ile Lys Thr Ile Cys Ala Leu Ile Cys Gly Arg Pro Ile Val
    50                  55                  60

Lys Pro Glu Tyr Phe Thr Glu Phe Leu Lys Ala Val Glu Ser Lys Lys
65                  70                  75                  80

Gln Pro Pro Gln Ile Glu Ser
                85

<210> SEQ ID NO 52
<211> LENGTH: 87
<212> TYPE: PRT
<213> ORGANISM: C. elegans

<400> SEQUENCE: 52

Ala Met Asn Pro Arg Phe Leu Leu Ser Val Ser Asn Met Asp Pro Gln
1               5                   10                  15

Arg Ala Ala Asp Leu Gln Glu Thr Ile Met Lys Leu Gly Gly Thr Ile
            20                  25                  30

Glu Arg Glu Phe Asn Lys Asp Val Thr His Leu Ile Ala Ser Asn Met
        35                  40                  45

Gln Arg Ala Pro Lys Val Leu Cys Ser Ile Ala Ala Gly Lys Trp Cys
    50                  55                  60

Leu Thr Pro Asp Tyr Val Thr Lys Ser Ala Glu Val Gly Arg Trp Leu
65                  70                  75                  80

Asp Glu Lys Ser Phe Glu Trp
                85

<210> SEQ ID NO 53
<211> LENGTH: 88
<212> TYPE: PRT
<213> ORGANISM: A. thaliana

<400> SEQUENCE: 53
```

```
Glu His Glu Pro Lys Phe Phe Ile Val Ser Gly Pro Arg Ser Gln Arg
 1               5                  10                  15

Asn Glu Tyr Gln Gln Ile Ile Arg Arg Leu Lys Gly Lys Cys Cys Arg
                20                  25                  30

Asp Ser His Gln Trp Ser Tyr Gln Ala Thr His Phe Ile Ala Pro Glu
                35                  40                  45

Ile Arg Arg Thr Glu Lys Phe Phe Ala Ala Ala Ser Gly Ser Trp
 50                  55                  60

Ile Leu Lys Thr Asp Tyr Val Ala Asp Ser Lys Glu Ala Gly Lys Leu
 65                  70                  75                  80

Leu Gln Glu Glu Pro Tyr Glu Trp
                85

<210> SEQ ID NO 54
<211> LENGTH: 84
<212> TYPE: PRT
<213> ORGANISM: Homo sapien

<400> SEQUENCE: 54

Glu Leu Thr Pro Phe Val Leu Phe Thr Gly Phe Glu Pro Val Gln Val
 1               5                  10                  15

Gln Gln Tyr Ile Lys Lys Leu Tyr Ile Leu Gly Gly Glu Val Ala Glu
                20                  25                  30

Ser Ala Gln Lys Cys Thr His Leu Ile Ala Ser Lys Val Thr Arg Thr
                35                  40                  45

Leu Lys Phe Leu Ala Ala Ile Ser Val Val Lys His Ile Val Thr Pro
 50                  55                  60

Glu Trp Leu Glu Glu Cys Phe Arg Cys Gln Lys Phe Ile Asp Glu Gln
 65                  70                  75                  80

Asn Tyr Ile Leu

<210> SEQ ID NO 55
<211> LENGTH: 86
<212> TYPE: PRT
<213> ORGANISM: Homo sapien

<400> SEQUENCE: 55

Arg Asp Gly Pro Leu Val Leu Ile Gly Ser Gly Leu Ser Ser Glu Gln
 1               5                  10                  15

Gln Lys Met Leu Ser Glu Leu Ala Val Ile Leu Lys Ala Lys Lys Tyr
                20                  25                  30

Thr Glu Phe Asp Ser Thr Val Thr His Val Val Pro Gly Val Gln
                35                  40                  45

Ser Thr Leu Lys Cys Met Leu Gly Ile Leu Asn Gly Cys Trp Ile Leu
 50                  55                  60

Lys Phe Glu Trp Val Lys Ala Cys Leu Arg Arg Lys Val Cys Glu Gln
 65                  70                  75                  80

Glu Glu Lys Tyr Glu Ile
                85

<210> SEQ ID NO 56
<211> LENGTH: 84
<212> TYPE: PRT
<213> ORGANISM: Homo sapien

<400> SEQUENCE: 56

Leu Gln Gly Val Val Val Val Leu Ser Gly Phe Gln Asn Pro Phe Arg
```

```
   1               5                  10                 15
Ser Glu Leu Arg Asp Lys Ala Leu Glu Leu Gly Ala Lys Tyr Arg Pro
                20                  25                  30
Asp Trp Thr Arg Asp Ser Thr His Leu Ile Cys Ala Phe Ala Asn Thr
                35                  40                  45
Pro Lys Tyr Ser Gln Val Leu Gly Leu Gly Arg Ile Val Arg Lys
                50                  55                  60
Glu Trp Val Leu Asp Cys His Arg Met Arg Arg Leu Pro Ser Arg
 65                 70                  75                  80
Arg Tyr Leu Ala

<210> SEQ ID NO 57
<211> LENGTH: 86
<212> TYPE: PRT
<213> ORGANISM: Mus musculus

<400> SEQUENCE: 57

Met Leu Asn Leu Val Leu Cys Phe Thr Gly Phe Arg Lys Lys Glu Glu
 1               5                  10                  15
Leu Val Lys Leu Val Thr Leu Val His His Met Gly Gly Val Ile Arg
                20                  25                  30
Lys Glu Cys Asn Ser Lys Val Thr His Leu Val Ala Asn Cys Thr Gln
                35                  40                  45
Gly Glu Lys Phe Arg Val Ala Val Ser Leu Gly Thr Pro Ile Met Lys
                50                  55                  60
Pro Glu Trp Ile Tyr Lys Ala Trp Glu Arg Arg Asn Glu Gln Cys Phe
 65                 70                  75                  80
Cys Ala Ala Val Asp Asp
                85

<210> SEQ ID NO 58
<211> LENGTH: 85
<212> TYPE: PRT
<213> ORGANISM: Homo sapien

<400> SEQUENCE: 58

Asn Lys Arg Met Ser Met Val Val Ser Gly Leu Thr Pro Glu Glu Phe
 1               5                  10                  15
Met Leu Val Tyr Lys Phe Ala Arg Lys His His Ile Thr Leu Thr Asn
                20                  25                  30
Leu Ile Thr Glu Glu Thr Thr His Val Val Met Lys Thr Cys Glu Arg
                35                  40                  45
Thr Leu Lys Tyr Phe Leu Gly Ile Ala Gly Gly Lys Trp Val Val Ser
                50                  55                  60
Tyr Phe Trp Val Thr Gln Ser Ile Lys Glu Arg Lys Met Leu Asn Glu
 65                 70                  75                  80
His Asn Phe Glu Val
                85

<210> SEQ ID NO 59
<211> LENGTH: 88
<212> TYPE: PRT
<213> ORGANISM: Saccharomyces cerevisiae

<400> SEQUENCE: 59

Val Phe Asp Lys Cys Ile Phe Val Leu Thr Ser Leu Phe Glu Asn Arg
 1               5                  10                  15
```

```
Glu Glu Leu Arg Gln Thr Ile Glu Ser Gln Gly Gly Thr Val Ile Glu
            20                  25                  30

Ser Gly Phe Ser Thr Leu Phe Asn Phe Thr His Pro Leu Ala Lys Ser
        35                  40                  45

His Leu Arg Ser Leu Lys Tyr Leu Glu Thr Leu Ala Leu Gly Trp Pro
    50                  55                  60

Thr Leu His Trp Lys Phe Ile Ser Ala Cys Ile Glu Lys Lys Arg Ile
65                  70                  75                  80

Val Pro His Leu Ile Tyr Gln Tyr
                85
```

<210> SEQ ID NO 60
<211> LENGTH: 84
<212> TYPE: PRT
<213> ORGANISM: Saccharomyces cerevisiae

<400> SEQUENCE: 60

```
Phe Lys Asn Cys Val Ile Tyr Ile Asn Gly Tyr Thr Lys Pro Gly Arg
 1               5                  10                  15

Leu Gln Leu His Glu Met Ile Val Leu His Gly Gly Lys Phe Leu His
            20                  25                  30

Tyr Leu Ser Ser Lys Lys Thr Val Thr His Ile Val Ala Ser Asn Leu
        35                  40                  45

Pro Leu Lys Lys Arg Ile Glu Phe Ala Asn Tyr Lys Val Val Ser Pro
    50                  55                  60

Asp Trp Ile Val Asp Ser Val Lys Glu Ala Arg Leu Leu Pro Trp Gln
65                  70                  75                  80

Asn Tyr Ser Leu
```

<210> SEQ ID NO 61
<211> LENGTH: 45
<212> TYPE: DNA
<213> ORGANISM: Homo sapien

<400> SEQUENCE: 61
caggacggca ggaaagaaaa caaatcttca aagggaaaac attta            45

<210> SEQ ID NO 62
<211> LENGTH: 46
<212> TYPE: DNA
<213> ORGANISM: Homo sapien

<400> SEQUENCE: 62
caggacggca ggaaagaaat cttcaaaggg aaaacattta tatttt           46

<210> SEQ ID NO 63
<211> LENGTH: 48
<212> TYPE: DNA
<213> ORGANISM: Homo sapien

<400> SEQUENCE: 63
caggacggca ggaaagaaat cwwctcwtsg aagrsatwtm atwttwtw          48

<210> SEQ ID NO 64
<211> LENGTH: 5
<212> TYPE: PRT
<213> ORGANISM: Artificial Sequence

```
<220> FEATURE:
<223> OTHER INFORMATION: Flexible polylinker

<400> SEQUENCE: 64

Gly Gly Gly Gly Ser
1               5
```